(12) United States Patent
Sergeev

(10) Patent No.: US 6,831,071 B2
(45) Date of Patent: Dec. 14, 2004

(54) SYNTHESIS OF BIOLOGICALLY ACTIVE COMPOUNDS IN CELLS

(76) Inventor: Pavel Sergeev, Herbstweg 63, 8050 Zürich (CH)

( * ) Notice: Subject to any disclaimer, the term of this patent is extended or adjusted under 35 U.S.C. 154(b) by 0 days.

(21) Appl. No.: 09/958,163

(22) PCT Filed: Apr. 8, 1999

(86) PCT No.: PCT/IB99/00616

§ 371 (c)(1),
(2), (4) Date: Oct. 3, 2001

(87) PCT Pub. No.: WO00/61775

PCT Pub. Date: Oct. 19, 2000

(65) Prior Publication Data

US 2003/0104389 A1 Jun. 5, 2003

(51) Int. Cl.[7] ........................ A61K 31/70; A01N 61/00; C07H 23/04; C12Q 1/68; C07K 7/00
(52) U.S. Cl. ................... 514/44; 514/1; 435/6; 435/7.1; 435/7.2; 530/300; 530/350; 536/23.1
(58) Field of Search ............................. 435/6, 7.1, 7.21; 530/300, 350; 514/1, 44; 536/23.1

(56) References Cited

PUBLICATIONS

Uhlmann et al. "Antisense Oligonucleotides: A New Therapeutic Principles." Chemical Reviews, vol. 90, No. 4, 1990, pp. 543–584.*
The Merck Index, Abstract 387 (1996), Amanitin.
Complementary Carrier Peptide Synthesis etc.; Proc. Natl. Acad. Sci. USA 1979 vol. 76, No. 1, p. 51–5.
Template–directed Ligation of Peptides to Oligonucleotides; Chem. Biol. 1996 vol. 3, No. 1, p. 49–56.
Template–Directed Synthesis of Acyclic Oligonucleotide Anal. J. Mol. Evol. 1988 vol. 28 No. 1–2, p. 3–6.
Molecular Cloning and In Vitro Expression of a cDNA Clone etc.; Mol. & Cell. Biol. vol. 5, No. 7, p. 1601–10, 1985.
The Merck Index, Abstract 2867, 1996, Dactinomycin.
Antitumor Agents LIV: The Effects of Daphnoretin etc.; J. Pharm. Sci. 1982 vol. 71, No. 7, 745–9.
A New Synthetic Method for 1–0–Acyl–B–D–Glucopyranoses etc.; Tetrahedron Letters, vol. 24, 1983, p. 2779–80.
The Merck Index, Abstract 6836 (1996) Ochratoxins.
The Merck Index, Abstract 3703 (1996) Ergotamine.

* cited by examiner

*Primary Examiner*—Jezia Riley
(74) *Attorney, Agent, or Firm*—William H. Eilberg

(57) ABSTRACT

This invention relates to a new method of synthesis of biologically active substances of determined structure directly in the cells of living organisms containing specific RNA or DNA molecules of determined sequence. The method is based on the hybridization of two or more oligomers bound with biologically inactive precursors of biologically active substances to specific RNA or DNA in vivo in the cells of living organisms. After hybridization of the oligomers to RNA or DNA the biologically inactive precursors bound to the 5' and/or 3' ends of the oligomers can interact with each other to make biologically active form of the substances. This changing of properties is due to chemical reactions which bind the biologically inactive precursors through a chemical bond into a biologically active form of the whole compound.

8 Claims, 14 Drawing Sheets

Drawings

Drawings

Fig. 3.

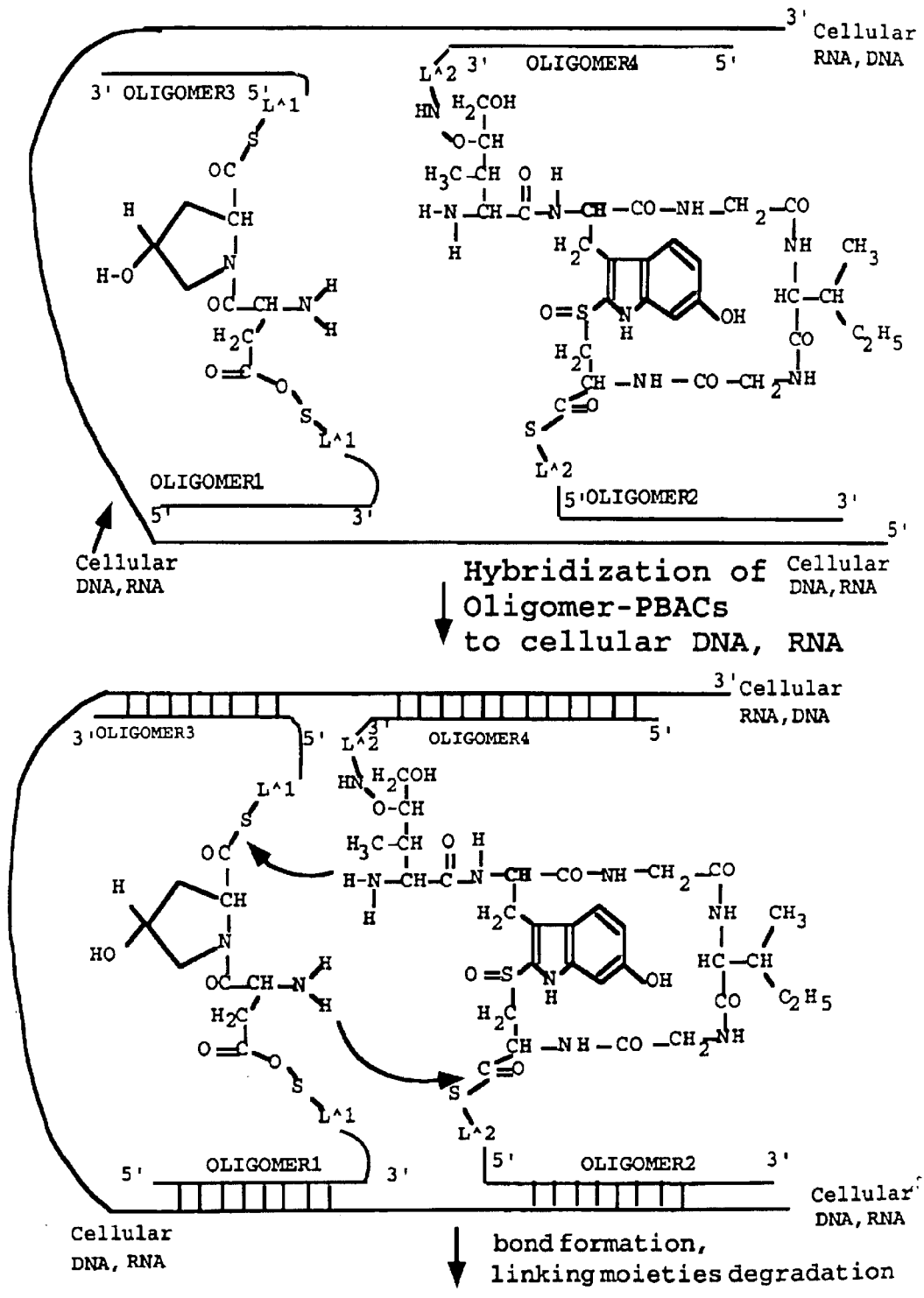
Fig. 4 (page 1)

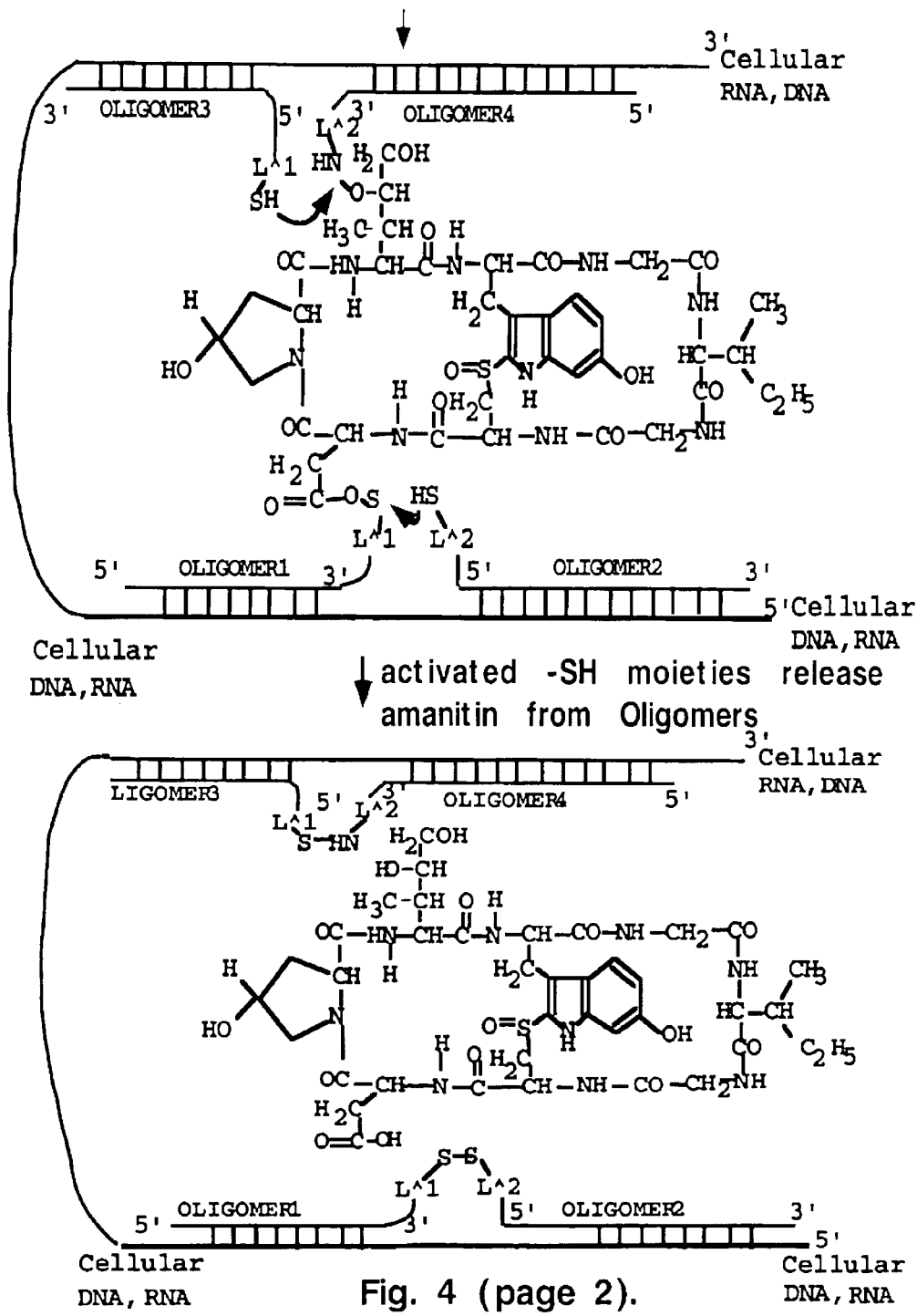
Fig. 4 (page 2).

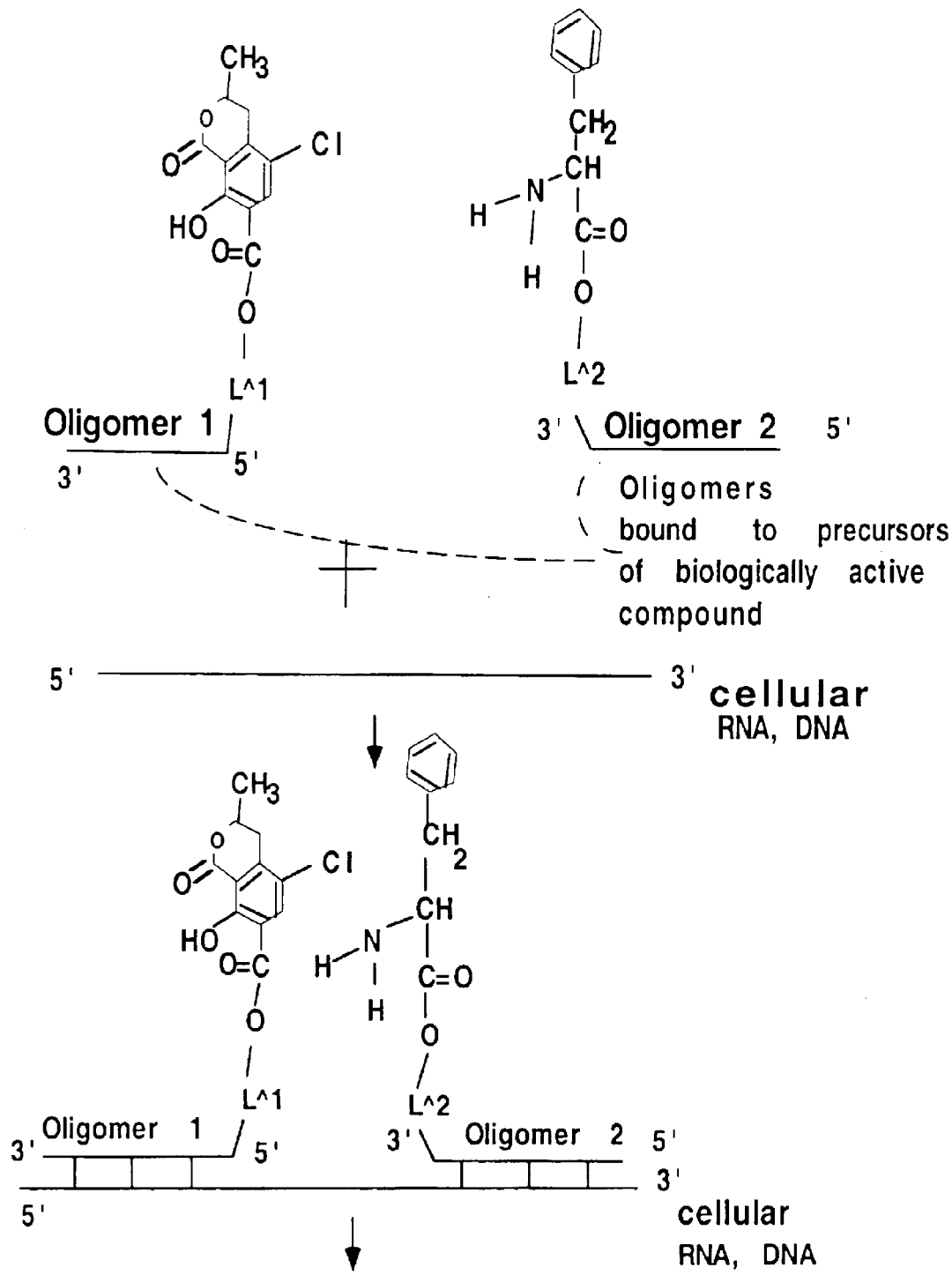
Fig. 6 (page 1)

Fig. 6 (page 2)

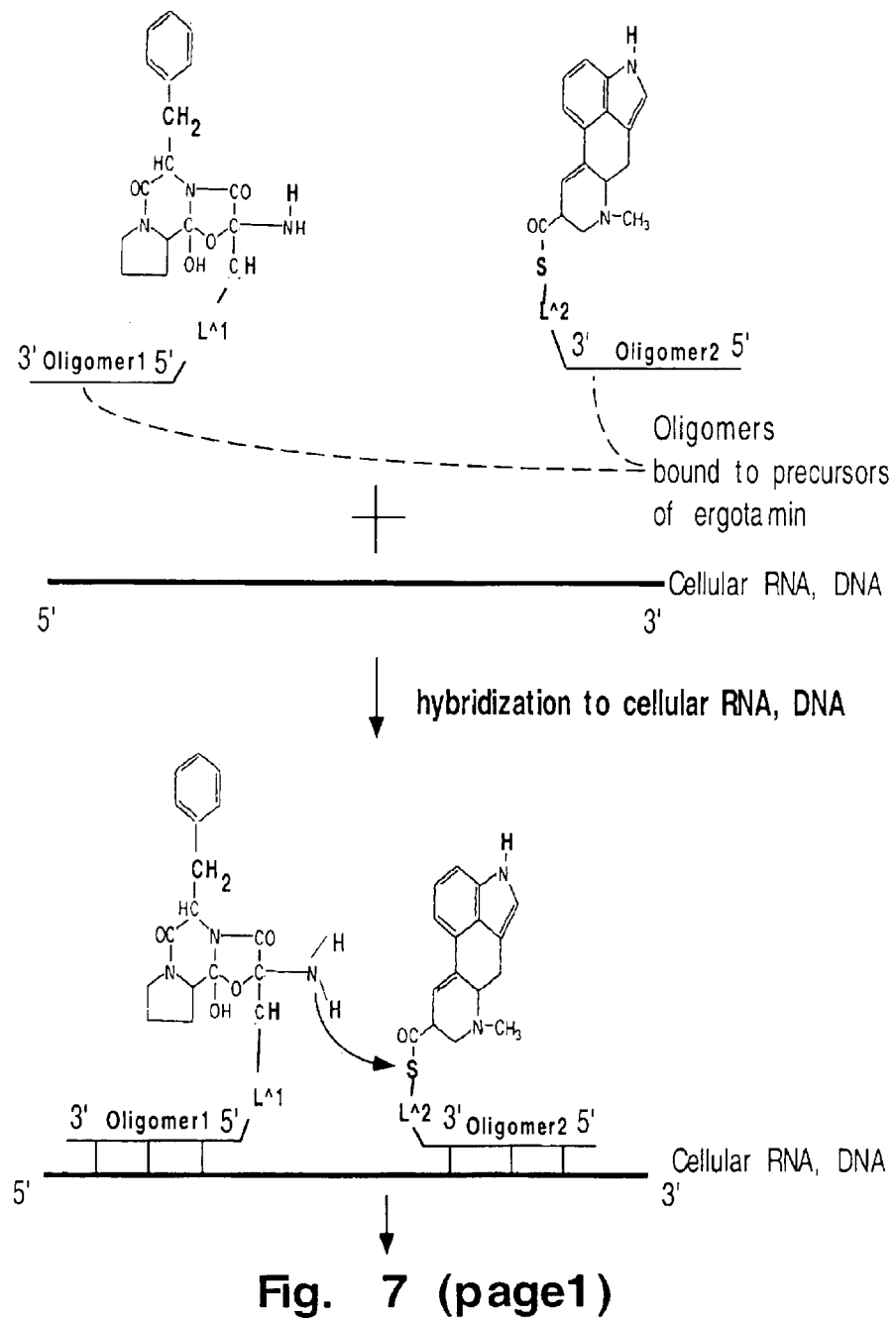
Fig. 7 (page1)

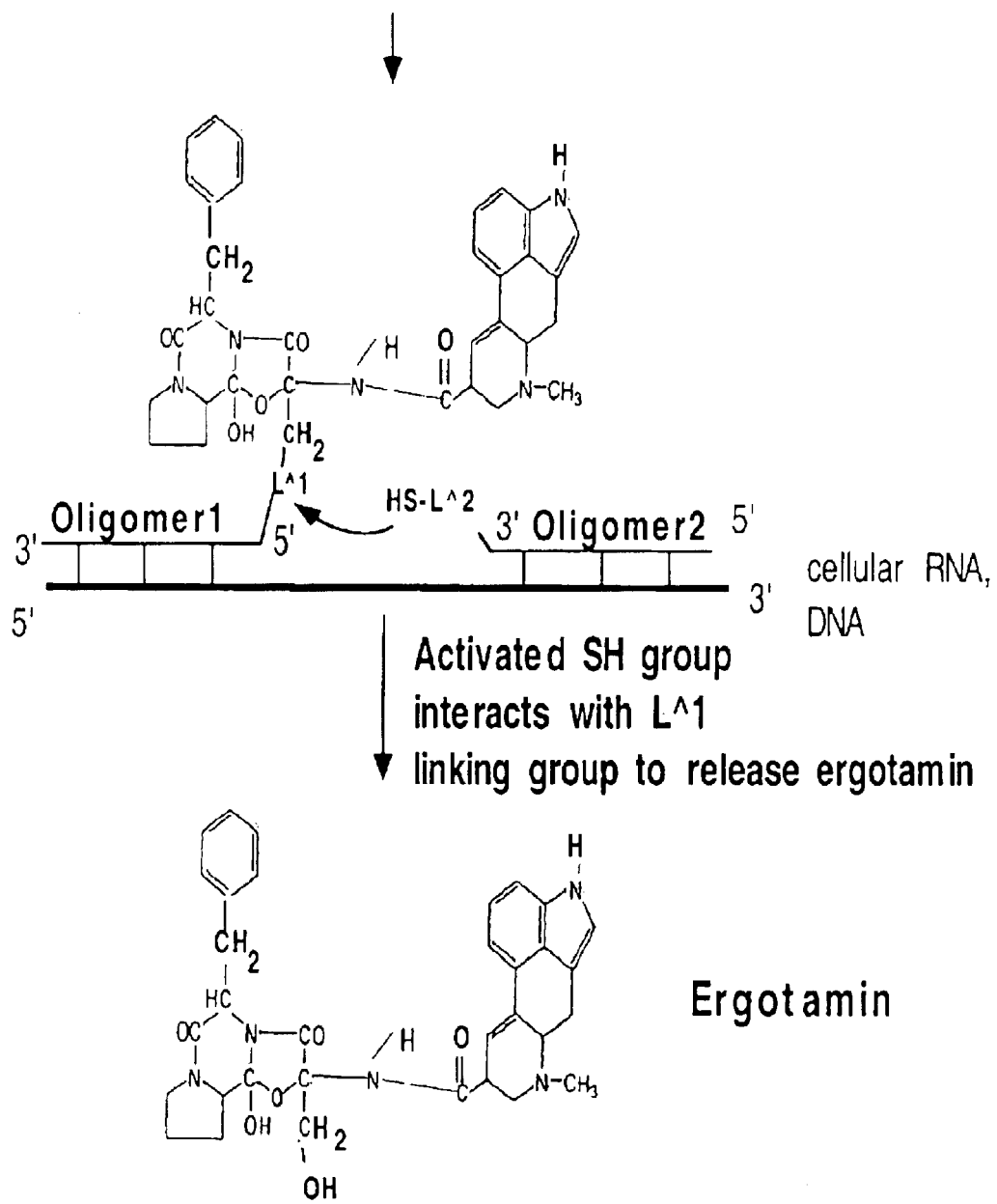
Fig. 7 (page 2)

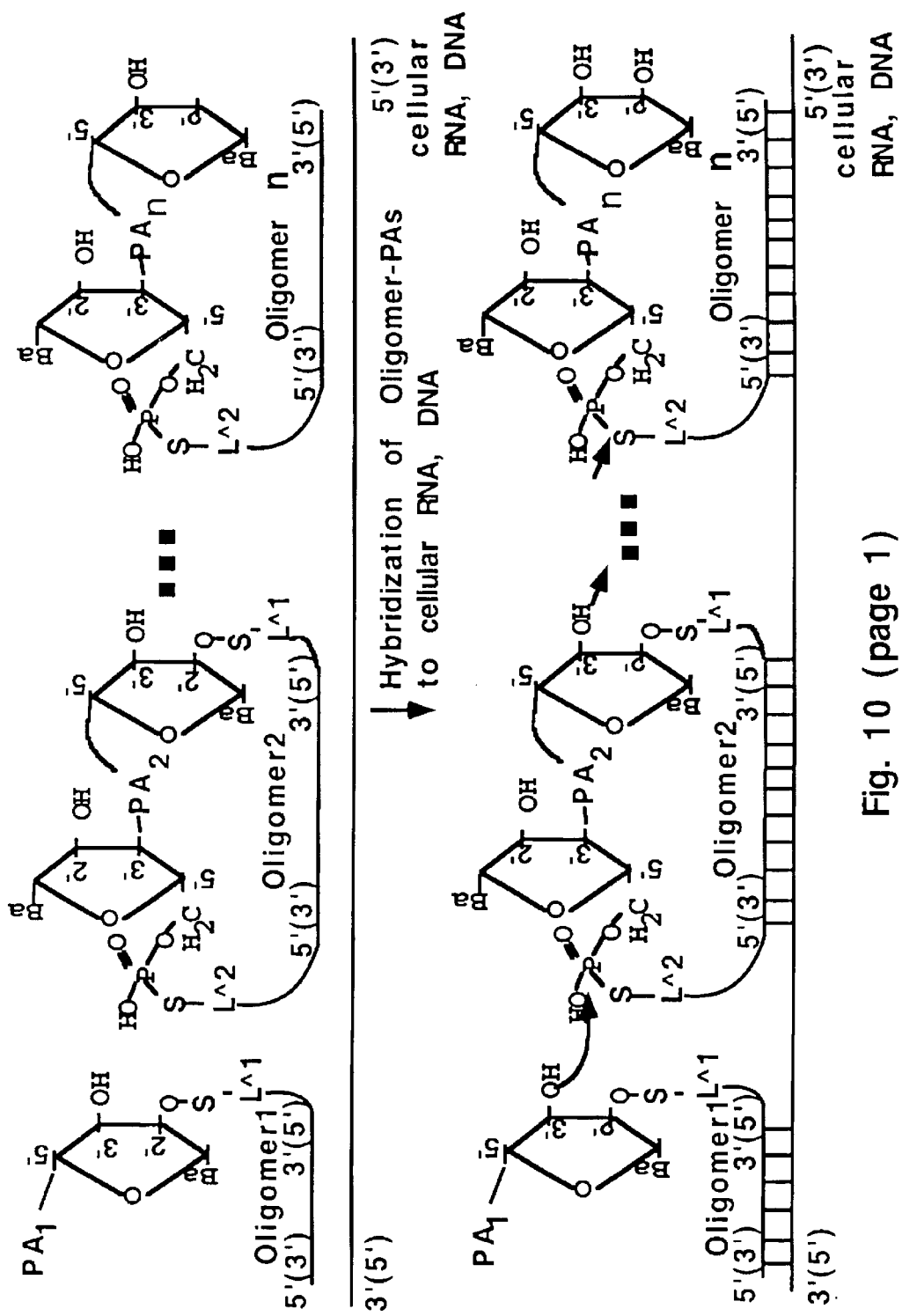
Fig. 10 (page 1)

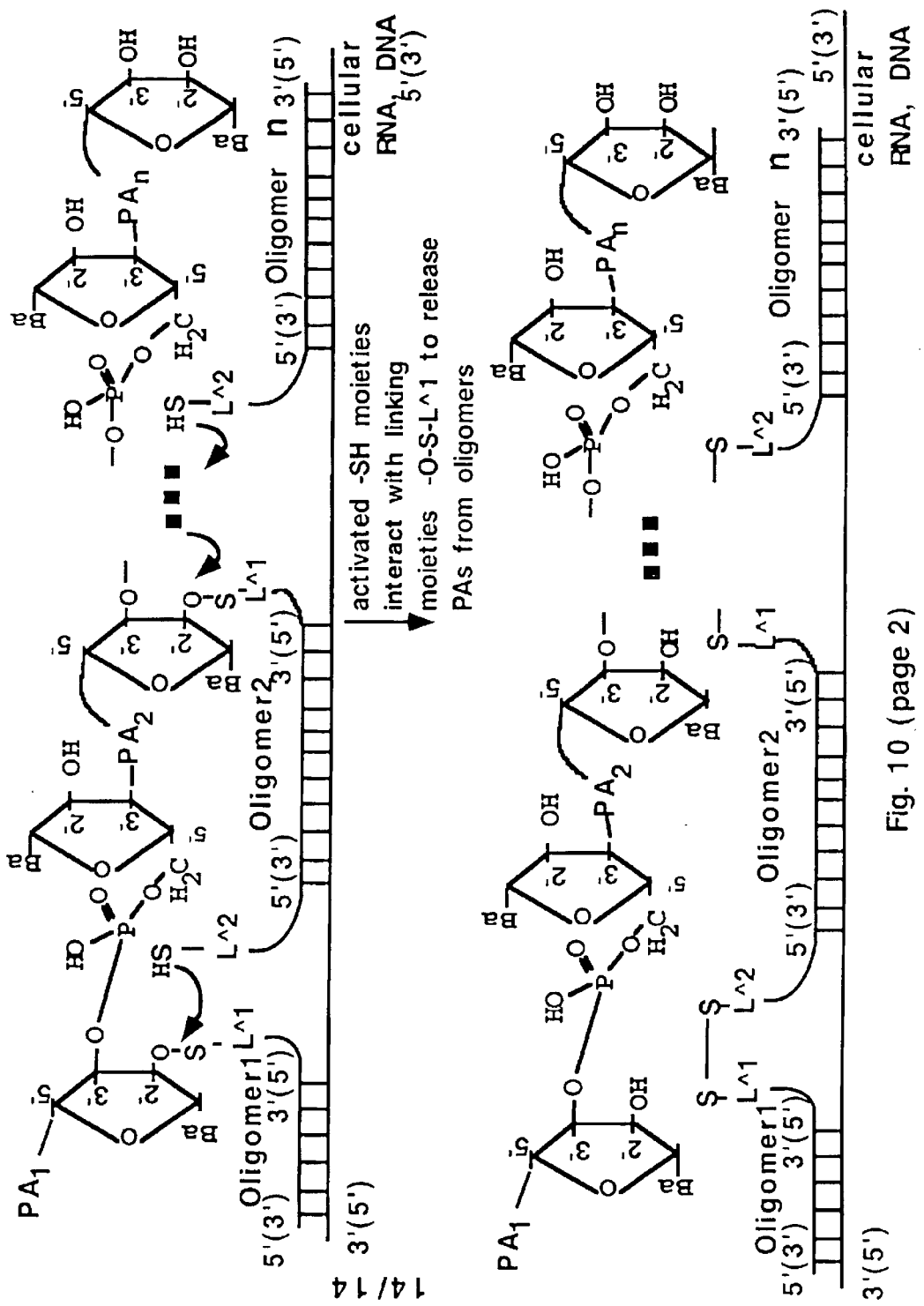
Fig. 10 (page 2)

SYNTHESIS OF BIOLOGICALLY ACTIVE COMPOUNDS IN CELLS

This application is a 371 of PCT/IB99/00616 filed Apr. 8, 1999.

| Technical field | |
|---|---|
| Int. Cl. | C07F 9/22; C07F 9/28; C07C 321/00; C07C 323/00 |
| U.S. Cl. | 560/147: 562/9; 562/10; 562/11 |
| Field of search | C07F 9/22; C07F 9/28; C07C 321/00; C07C 323/00 |

| References cited U.S. patent documents | | |
|---|---|---|
| 5,562,350 | July 1997 | Watanabe et. al., |
| 5,177,198 | January 1993 | Spielvogel et. al., |
| 5,594,121 | January 1994 | Froehler et. al., |
| 5,599,922 | February 1997 | Grjasnov et. al., |
| 5,521,302 | May 1996 | Cook Ph.D. |
| 5,177,064 | January 1993 | Bodor N.S. |
| 5,571,937 | November 1996 | Kyoichi A. Watanabe. |

OTHER REFERENCES

Walder, J. a., et al., (1979), Complementary carrier peptide synthesis: General strategy and implications for prebiotic origin of peptide synthesis. Proc.Natl.Acad.Sci USA, vol. 76, pp. 51–55.
Ebata K., et al. (1995), Nucleic acids hyridization accompanied with excimer formation from two pyrene-labeled probes.
Photochemistry and Photobiology, vol. 62(5), pp. 836–839.
Nielsen P. E., (1995), DNA analogues with non phosphodiester backbones. Annu.Rev.Biophys. Biomol.Struct. vol.24, pp. 167–83.
Tam J. P., et al., (1995), Peptide synthesis using unprotected peptides through orthogonal coupling methods.
Proc.Natl.Acad.Sci. USA, vol.92, pp.12485–12489.
Uhlmann G. A. et al., (1990) Antisense Oligonucleotides: A New Therapeutic principle, Chemical Rev., vol. 90, pp.543–584.
Moser H. E. and Dervan P. B., (1987), Sequence-specific cleavage of double helical DNA by triple helix formation. Science, vol. 238, pp.645–650.
Tulchinsky E. et al., (1992) "Transcriptional analsis of the mts 1 gene with the specific reference to 5' flanking sequences. Proc.Natl.Acad.Sci USA, vol. 89, pp. 9146–9150.

BACKGROUND ART

The use of oligo(ribo)nucleotides and their analogues as anticancer and antiviruses theraupetic agents was first proposed several years ago. (Uhlmann, 1990) The great number of different modifications of the oligonucleotides and the methods of their use have since been developed.

Two basic interactions between oligonucleotides and nucleic acids are known (Moser and Dervan, 1987)

1. Watson-Crick base pairing (Duplex structure)
2. Hoogsten base pairing (Triplex structure)

Oligonucleotides can form duplex and/or triplex structures with DNA or RNA of cells and so regulate transcription or translation of genes.

It has been proposed that different substances which can cleave target nucleic acids or inhibit important cellular enzymes could be coupled to oligomers. The use of such conjugates as therapeutic agents has been described.(U.S. Pat. Nos., 5,177,198; 5,652,350).

Other methods are based on the coupling of different biologically active substances, such as toxins, to monoclonal antibodies which can then recognise receptors or other structures of cancer cells, or cells infected with viruses. Monoclonal antibodies can then specifically recognise cancer cells and in this way transport toxins to these cells. But these methods are inefficient due to the high level of nonspecific interactions between antibodies and other cells, which leads to delivary of the toxins or other biologically active compounds to the wrong cells.

In 1979 I. M. Klotz and co-authors proposed a method for complementary carrier peptide synthesis based on a template-directlyed scheme (J. A. Walder et al. 1979) The method proposed the synthesis of peptides on a solid support using unprotected amino acids, and the subsequent hybridization of oligonucleotides on the template. This method was established only for synthesis of peptides in vitro using solid supports of a different origin, and involved many synthesis steps to obtain peptides of the determined structure.

M. Masuko and co-authors proposed another method for in vitro detection of specific nucleic acids by excimer formation from two pyrene-labeled probes (Ebata, K. et al. 1995).

My invention allows the synthesis of different BACs of determined structure directly in living organisms only in cells which have specific RNA or DNA sequences. In this way, BACs will be delivered only to those cells where specific nucleic acids are produced.

DISCLOSURE OF INVENTION

Definitions

"Nulceomonomer"

The term "nucleomonomer" means a "Base" chemically bound to "S" moieties. Nucleomonomers can include nucleotides and nucleosides such as thymine, cytosine, adenine, guanine, diaminopurine, xanthine, hypoxanthine, inosine and uracil. Nucleomonomers can bind each other to form oligomers which can be specifically hybridised to nucleic acids in a sequence and direction specific manner.

The "S" moieties used herein include D-ribose and 2'-deoxy-D-ribose. Sugar moieties can be modified so that hydroxyl groups are replaced with a heteroatom, aliphatic group, halogen, ethers, amines, mercapto, thioethers and other groups. The pentose moiety can be replaced by a cyclopentane ring, a hexose, a 6-member morpholino ring; it can be aminoacids analogues coupled to base, bicyclic riboacetal analogues, morpholino carbamates, alkanes, ethers, amines, amides, thioethers, formacetals, ketones, carbamates, ureas, hydroxylamines, sulfamates, sulfamides, sulfones, glycinyl amides other analogues which can replace sugar moieties. Oligomers obtained from the mononucleomers can form stabile duplex and triplex structures with nucleic acids. (Nielsen P. E. 1995, U.S. Pat. No. 5,594,121).

"Base"

"Base" (designated as "Ba") includes natural and modified. purines and pyrimidines such as thymine, cytosine, adenine, guanine, diaminopurine, xanthine, hypoxanthine, inosine, uracil, 2-aminopyridine, 4,4-ethanocytosine, 5-methylcytosine, 5-methyluracil, 2-aminopyridine and 8-oxo-N(6)-methyladenine and their analogues. These may include, but are not limited to adding substituents such as —OH, —SH, —SCH(3), —OCH(3), —F, —Cl, —Br, —NH(2), alkyl, groups and others. Also, heterocycles such as triazines are included.

"Nucleotide"

Nucleotide as used herein means a base chemically bound to a sugar or sugar analogues having a phosphate group or phosphate analog.

"Oligomer"

Oligomer means that at least two "nucleomonomers" (defined above) are chemically bound to each other. Oligomers can be oligodeoxyribonucleotides consisting of from 2 to 200 nucleotides, oligoribonucleotides consisting of from 2 to 200 nucleotides, or mixtures of oligodeoxyribonucleotides and oligoribonucleotides. The nucleomonomers can bind each other through phosphodiester groups, phosphorothioate, phosphorodithioate, alkylphosphonate, boranophosphates, acetals, phosphoroamidate, bicyclic riboacetal analogues morpholino carbamates, alkanes, ethers, amines, amides, thioethers, formacetals, ketones, carbamates, ureas, hydroxylamines, sulfamates, sulfamides, sulfones, glycinyl amides and other analogues which can replace phosphodiester moiety. Oligomers are composed of mononucleomers or nucleotides. Oligomers can form stable duplex structures via Watson-Crick base pairing with specific sequences of DNA, RNA, mRNA, rRNA and tRNA in vivo in the cells of living organisms or they can form stable triplex structures with double stranded DNA or dsRNA in vivo in the cells of living organisms.

"Alkyl"

"Alkyl" as used herein is a straight or branched saturated group having from 1 to 10 carbon atoms. Examples include methyl, ethyl, propyl, isopropyl, butyl, isobutyl, tert-butyl, pentyl, hexyl and the like.

"Alkenyl"

"Alkenyl" as used herein is a straight- or branched-chain olefinically-unsaturated group having from two to 25 carbon atoms. The groups contain from one to three double bounds. Examples include vinyl (—CHdbdCH(2), 1-propenyl (—CHdbdCH—CH(3)), 2-methyl-1-propenyl (—CHdbdC(CH(3))—CH(3)) and the like "Alkynyl"

"Alkynyl" as used herein is a straight or branched acetynically-unsaturated groups having from two to 25 carbon atoms. The groups contain from one to three triple bounds. Examples include 1-alkynyl groups include ethynyl (—CtbdCH), 1-propynyl (—CtbdC—CH(3)), 1-butynyl (—CtbdC—CH(2 —CH(3)), 3-methyl-butynyl (—CtbdC—CH(CH(3)) —CH(3)), 3,3-dimethyl-butynyl (—CtbdC—C(CH(3))(3)), 1-pentynyl (—CtbdC—CH(2, —CH(2 —CH(3)) and 1,3-pentadiynyl (—CtbdC—CtbdC—CH(3)) and the like.

"Aryl"

"Aryl" as used herein includes aromatic groups having from 4 to 10 carbon atoms. Examples include phenyl, naphtyl and like this.

"Heteroalkyl"

"Heteroalkyl" as used herein is an alkyl group in which 1 to 8 carbon atoms are replaced with N (nitrogen), S (sulfur) or O (oxygen) atoms. At any carbon atom there can be one to three substituents. The substituents are selected from: —OH, —SH, —SCH$_3$, —OCH$_3$, halogen, —NH$_2$, —NO$_2$, —S(O)—, —S(O)(O)—, —O—S(O)(O)—O—, —O—P(O)(O)—O—, —NHR. Here R is alkyl, alkenyl, aryl, heteroaryl, alkynyl, heterocyclic, carbocyclic and like this groups.

"Heteroalkenyl"

"Heteroalkenyl" as used herein is an alkenyl group in which 1 to 8 carbon atoms are replaced with N (nitrogen), S (sulfur) or O (oxygen) atoms. At any carbon atom there can be one to three substituents. The substituents are selected from group —OH, —SH, —SCH$_3$, —OCH$_3$, halogen, —NH$_2$, NO$_2$, —S(O)—, —S(O)(O)—, —O—S(O)(O)—O—, —O—P(O)(O)—O—, —NHR. Here R is alkyl, alkenyl, aryl, heteroaryl, alkynyl, heterocyclic, carbocyclic and like this groups.

"Heteroalkynyl"

"Heteroalkynyl" as used herein is an alkynyl group in which 1 to 8 carbon atoms are replaced with N (nitrogen), S (sulfur) or O (oxygen) atoms. At any carbon atom there can be one to three substituents. The substituents are selected from group —OH, —SH, —SCH$_3$, —OCH$_3$, halogen, —NH$_2$, NO$_2$, —S(O)—, —S(O)(O)'—, —O—S(O)(O)—O—, —O—P(O)(O)—O—, —NHR. Here R is alkyl, alkenyl, aryl, heteroaryl, alkynyl, heterocyclic, carbocyclic and like this groups.

"Heteroaryl"

"Heteroaryl" as used herein means an aromatic radicals comprising from 5 to 10 carbon atoms and additionally containing from and to three heteroatoms in the ring selected from group S, O or N. The examples include but not limited to: furyl, pyrrolyl, imidazolyl, pyridyl indolyl, quinolyl, benzyl and the like. One to three carbon atoms of aromatic group can have substituents selected from —OH, —SH, —SCH$_3$, —OCH$_3$, halogen, —NH$_2$, NO$_2$, —S(O)—, —S(O)(O)—, —O—S(O)(O)—O—, —O—P(O)(O)—O—, —NHR, alkyl group. Here R is alkyl, alkenyl, aryl, heteroaryl, alkynyl, heterocyclic, carbocyclic or similar groups.

"Cycloheteroaryl"

"Cycloheteroaryl" as used herein means a group comprising from 5 to 25 carbon atoms from one to three aromatic groups which are combined via a carbocyclic or heterocyclic ring. An illustrative radical is fluorenylmethyl. One to two atoms in the ring of aromatic groups can be heteroatoms selected from N, O or S. Any carbon atom of the group can have substituents selected from —OH, —SH, —SCH$_3$, —OCH$_3$, halogen, —NH$_2$, NO$_2$, —S(O)—, —S(O)(O)—, —O—S(O)(O)—O—, —O—P(O)(O)—O—, —NHR, alkyl group. Here R is alkyl, alkenyl, aryl, heteroaryl, alkynyl, heterocyclic and carbocyclic and like this groups.

"Carbocyclic"

"Carbocyclic" as used herein designates a saturated or unsaturated ring comprising from 4 to 8 ring carbon atoms. Carbocyclic rings or groups include cyclopentyl, cyclohexyl and phenyl groups. Any carbon atom of the group can have substituents selected from —OH, —SH, —SCH$_3$, —OCH$_3$, halogen, —NH$_2$, NO$_2$, —S(O)—, —S(O)(O)—, —O—S(O)(O)—O—, —O—P(O)(O)—O—, —NHR, alkyl group. Here R is alkyl, alkenyl, aryl, heteroaryl, alkynyl, heterocyclic and carbocyclic and like this groups.

"Heterocyclic Ring"

"Heterocyclic ring" as used herein is a saturated or unsaturated ring comprising from 3 to 8 ring atoms. Ring atoms include C atoms and from one to three N, O or S atoms. Examples include pyrimidinyl, pyrrolinyl, pyridinyl and morpholinyl. At any ring carbon atom there can be substituents such as —OH, —SH, —SCH$_3$, —OCH$_3$, halogen, —NH$_2$, NO$_2$, —S(O)—, —S(O)(O)—, —O—S(O)(O)—O—, —O—P(O)(O)—O—, —NHR, alkyl. Where R is alkyl, alkenyl, aryl, heteroaryl, alkynyl, heterocyclic and carbocyclic and like this groups.

"Hybridization"

"Hybridization" as used herein means the formation of duplex or triplex structures between oligomers and ssRNA, ssDNA, dsRNA or dsDNA molecules. Duplex structures are based on Watson-Crick base pairing. Triplex structures are formed through Hoogsteen base interactions. Triplex structures can be parallel and antiparallel.

The word "halogen" means an atom selected from the group consisting of F (fluorine), Cl (clorine), Br (bromine) and I (iodine)

The word "hydroxyl" means an —OH group:

The word "carboxyl" means an —COOH function.

The word "mercapto" means an —SH function.

The word "amino" means—NH(2) or —NHR. Where R is alkyl, alkenyl, aryl, heteroaryl, heteroalkyl, alkynyl, heterocyclic, carbocyclic and like this groups.

"Biologically Active Compounds (BACs)"

"Biologically active compound as defined herein include but are not limited to:

1) biologically active peptides and proteins consisting of natural aminoacids and their synthetic analogues L, D, or DL configuration at the alpha carbon atom selected from valine, leucine, alanine, glycine, tyrosine, tryptophan, tryptophan isoleucine, proline, histidine, lysin, glutamic acid, methionine, serine, cysteine, glutamine phenylalanine, methionine sulfoxide, threonine, arginine, aspartic acid, asparagin, phenylglycine, norleucine, norvaline, alpha-aminobutyric acid, O-methylserine, O-ethylserine, S-methylcysteine, S-benzylcysteine, S-ethylcysteine, 5,5,5-trifluoroleucine and hexafluoroleucine. Also included are other modifications of aminoacids which include but are not limited to, adding substituents at carbon atoms such as —OH, —SH, —$SCH_3$, —$OCH_3$, —F, —Cl, —Br, —$NH_2$. The peptides can be also glycosylated and phosphorylated.
2) Cellular proteins which include but are not limited to: enzymes, DNA polymerases, RNA polymerases, esterases, lipases, proteases, kinases, transferases, transcription factors, transmembrane proteins, membrane proteins, cyclins, cytoplasmic proteins, nuclear proteins, toxins and like this.
3) Biologically active RNA such as mRNA, ssRNA, rsRNA and like this.
4) Biologically active alkaloids and their synthetic analogues with added substituents at carbon atoms such as —OH, —SH, —$SCH_3$, —$OCH_3$, —F, —Cl, —Br, —$NH_2$, alkyl straight and branched.
5) Natural and synthetic organic compounds which can be:

a) inhibitors and activators of the cellular metabolism;
   b) cytolitical toxins;
   c) neurotoxins;
   d) cofactors for cellular enzymes;
   e) toxins;
   f) inhibitors of the cellular enzymes.

"Precursor(s) of Biologically Active Substances (PBAC (s))"

"Precursors of biologically active compounds (PBACs)" as used herein are biologically inactive precursors of BACs which can form whole BACs when bound to each other through chemical moiety(ies) "m" or simultaneously through chemical moieties "m" and "m^1". "m" and "m^1" are selected independently from: —S—S—, —O—, —NH—C(O)—, —C(O)—NH—, —C(O)—, —NH—, dbdN—, —C(O)O—, —C(O)S—, —S—, —C(S)S—, —C(S)O—, —N═N—.

Biologically active peptides and proteins are synthesized from shorter biologically inactive peptides. These shorter peptides as used herein are also biologically inactive precursors of biologically active compounds.

Biologically active RNAs can be synthesized from biologically inactive oligoribonucleotides.

"Oligomer-PBAC"

"Oligomer-PBAC" as used herein means a precursor of a BAC (PBAC) which is chemically bound at the first and/or last mononucleomer at the 3' and/or 5' ends of the oligomer through the chemical moieties L^1 and/or L^2. Chemical moieties L^1 and L^2 can be bound directly to a base or to a sugar moiety or to sugar moiety analogues or to phosphates or to phosphate analogues, "$Oligomer_n$-$PA_n$"

"$Oligomer_n$-$PA_n$" as used herein means the precursor of a biologically active protein or RNA which is chemically bound at the first and/or last mononucleomer at the 3' and/or 5' ends of the oligomer through the chemical moieties L^1 and/or L^2. n means the ordinal number of the oligomer of PA. PAs are biologically inactive peptides or biologically inactive oligoribonucleotides. Wherein n is selected from 2 to 300.

a) In Formulas 1 to 4 PBACs are designated as "A" and "B"

A-m-B is equal to a whole BAC "T"

"m" is selected independently from —S—S—, —O—, —NH—C(O)—, —C(O)—NH—, —C(O)—, —NH—, dbdN—, —C(O)O—, —C(O)S—, —S—, —C(S)S—, —C(S)O, —N═N—.

A-O—B is equal to a whole BAC "T"
A-NH—C(O)—B is equal to a whole BAC "T"
A-C(O)—NH—B is equal to a whole BAC "T"
A-C(O)—B is equal to a whole BAC "T"
A-NH—B is equal to a whole BAC "T"
A-dbdN—B is equal to a whole BAC "T"
A-C(O)O—B is equal to a whole BAC "T"
A-C(O)S—B is equal to a whole BAC "T"
A-C(S)S—B is equal to a whole BAC "T"
A-S—S—B is equal to a whole BAC "T"
A-C(S)O—B is equal to a whole BAC "T"
A-N═N—B is equal to a whole BAC "T"

b) Biologically active compounds can be formed through moieties "m" and "m^1". "m" and "m^1" are selected independently from: —S—S—, —O—, —NH—C(O)—, —C(O)—NH—, —C(O)—, —NH—, dbdN—, —C(O)O—, —C(O)S—, —S—, —C(S)S—, —C(S)O, —N═N—, so that

is equal to biologically active compound "T"

a BAC is represented on figure c) In Formulas 5 to 7, precursors of BACs (PBACs) are designated as "$PA_n$", where n is selected from 2 to 300. "PA" are peptides consisting of from 2 to 100 amino acids or oligoribonucleotides consisting of from 2 to 50 ribonucleotides.

{$PA_1$-m-$PA_2$-m-$PA_3$-m- . . . -m-$PA_{n-3}$-m-$PA_{n-2}$-m-$PA_{n-1}$-m-$PA_n$} is equal to BAC. BACs in this case are proteins or RNAs. Proteins can be enzymes, transcription factors, ligands, signaling proteins, transmembrane proteins, cytolitical toxins, toxins, cytoplasmic proteins, nuclear proteins and the like.

DETAILED DISCLOSURE OF THE INVENTION

This invention relates to the synthesis of biologically active compounds directly in the cells of living organisms. This is achieved by the hybridization of two or more oligomers to cellular RNA or DNA. These oligomers are bound to biologically inactive PBACs (oliogmer-PBACs) containing chemically active groups.

BAC can be synthesized only in those cells of living organisms which have specific RNA or DNA molecules of a determined sequence.

The principle Formulas of the invention are represented below:

Formula 1.

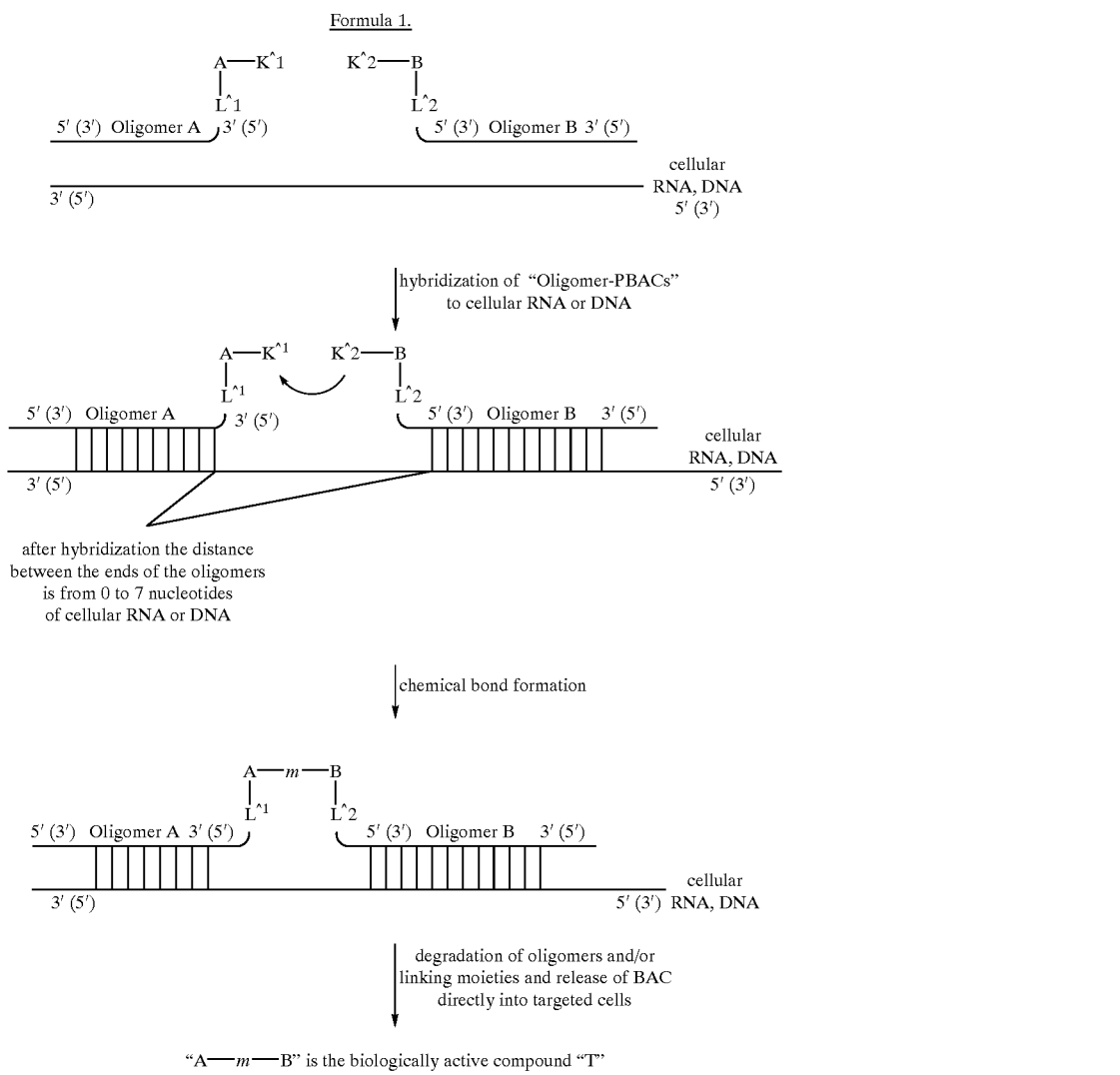

"A—m—B" is the biologically active compound "T"

After hybridization of the "Oligomer-PBACs" "A" and "B" to cellular RNA, DNA or dsDNA, the chemically active groups K^1 and K^2 of the oligomer-PBACs "A" and "B" interact with each other to form the chemical moiety "m", which combines PBACs "A" and "B" into one active molecule of biologically active compound "T". The degradation of the oligomers and/or linking moieties L^1 and L^2 by cellular enzymes or hydrolysis leads to the release of the synthesized BAC "T" directly into the targeted cells. After hybridization of the oligomer-PBACs to cellular RNA or DNA the distance between the 3' or 5' ends of the oligomer A and 5' or 3' ends of the oligomer B is from 0 to 7 nucleotides of cellular RNA, DNA or dsDNA.

Formula 2.

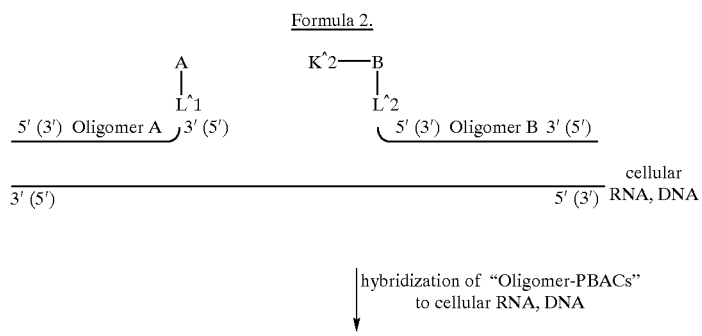

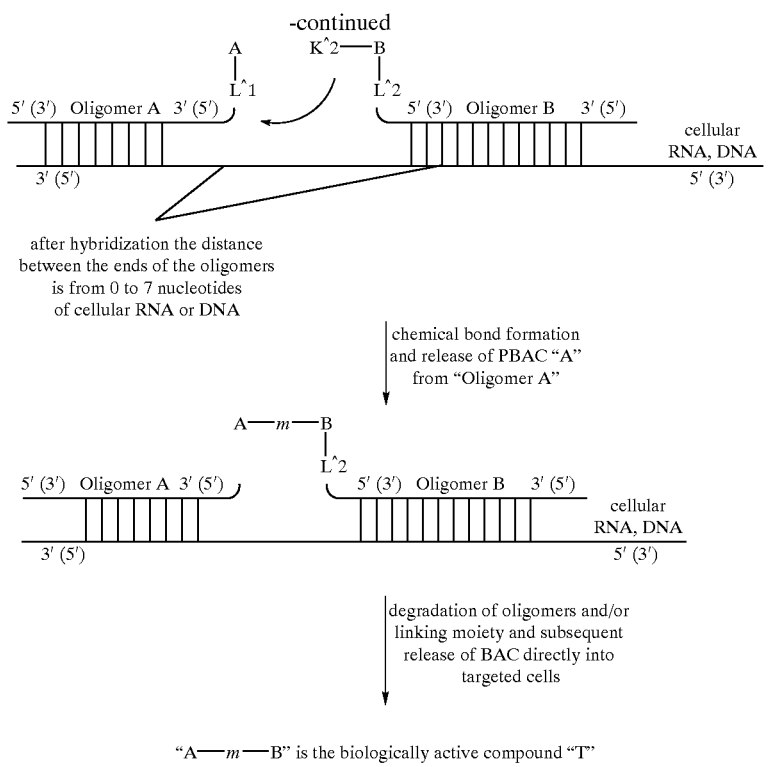

After hybridization of the "oligomer-PBACs" "A" and "B" to cellular RNA, DNA or dsDNA the chemically active group K^2 of the oligomer-PBAC "B" interacts with the linking moiety L^1 of the oligomer-PBAC "A" to combine the PBACs through the chemical moiety "m" into one active molecule of biologically active compound "T" with the subsequent release of one PBAC "B" from the oligomer. The degradation of the oligomer and/or linking moieties L^1 by cellular enzymes or hydrolysis leads to the release of synthesized BAC "T" directly into the targeted cells.

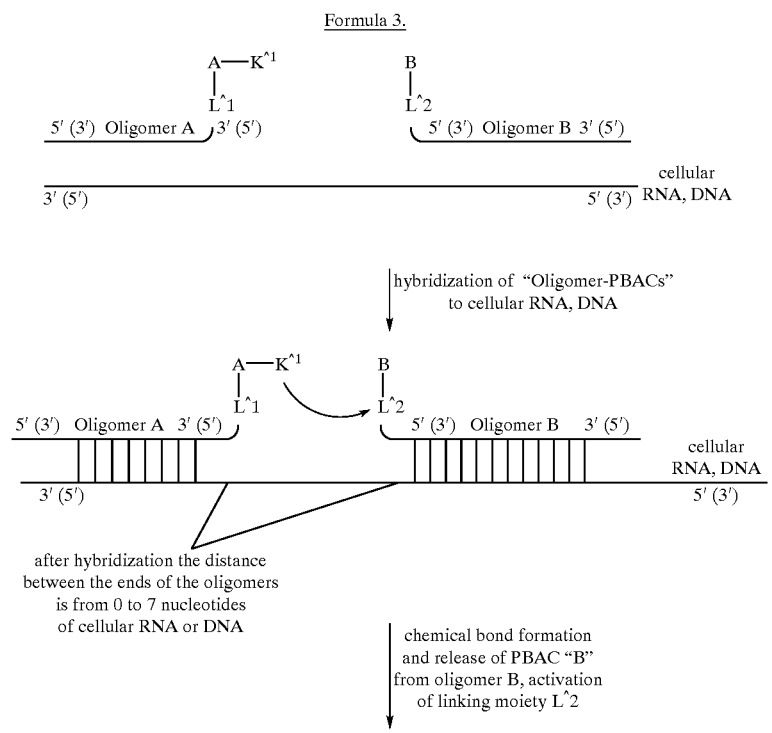

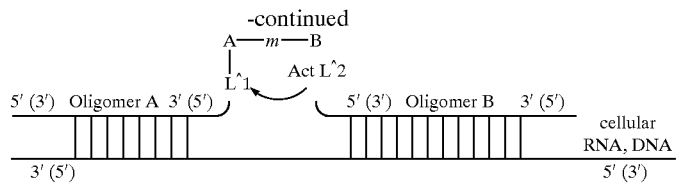

"A—m—B" is equal to the biologically active compound "T"

The chemically active group $K^1$ of the oligomer-PBAC A interacts with the linking moiety $L^2$ to combine the PBACs through the chemical moiety "m" into one active molecule of the biologically active compound "T" with the subsequent release of one PBAC "B" from oligomer "B" and the activation of the chemical moiety $L^2$. After activation, $L^2$ interacts with the linking moiety $L^1$ to release the biological compound "T" from the oligomer directly into targeted cells.

After hybridization, of the "oligomer-PBACs" "A" and "B" to cellular RNA, DNA or dsDNA, the chemically active group $K^2$ of the oligomer-PBAC "B" interacts with the linking moiety $L^1$ of the oligomer-PBAC "A" to combine the PBACs through the chemical moiety "m". At the same time the chemically active group $K^1$ of the oligomer-PBAC "A" interacts with the linking moiety $L^2$ of the oligomer-PBAc "B" to form chemical moiety $m^1$. Which together with chemical moiety m combines two "Oligomer-PBACs"

Formula 4.

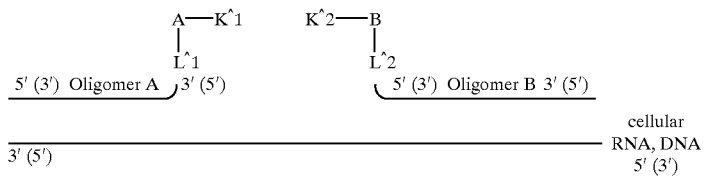

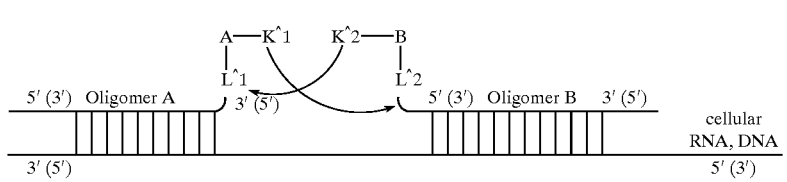

into one active molecule of biologically active compound "T", with the release of BAC from the oligomer.

"PA$_n$"s into one active molecule of the biologically active compound "PR" which consists of n PA$_n$ so that compound

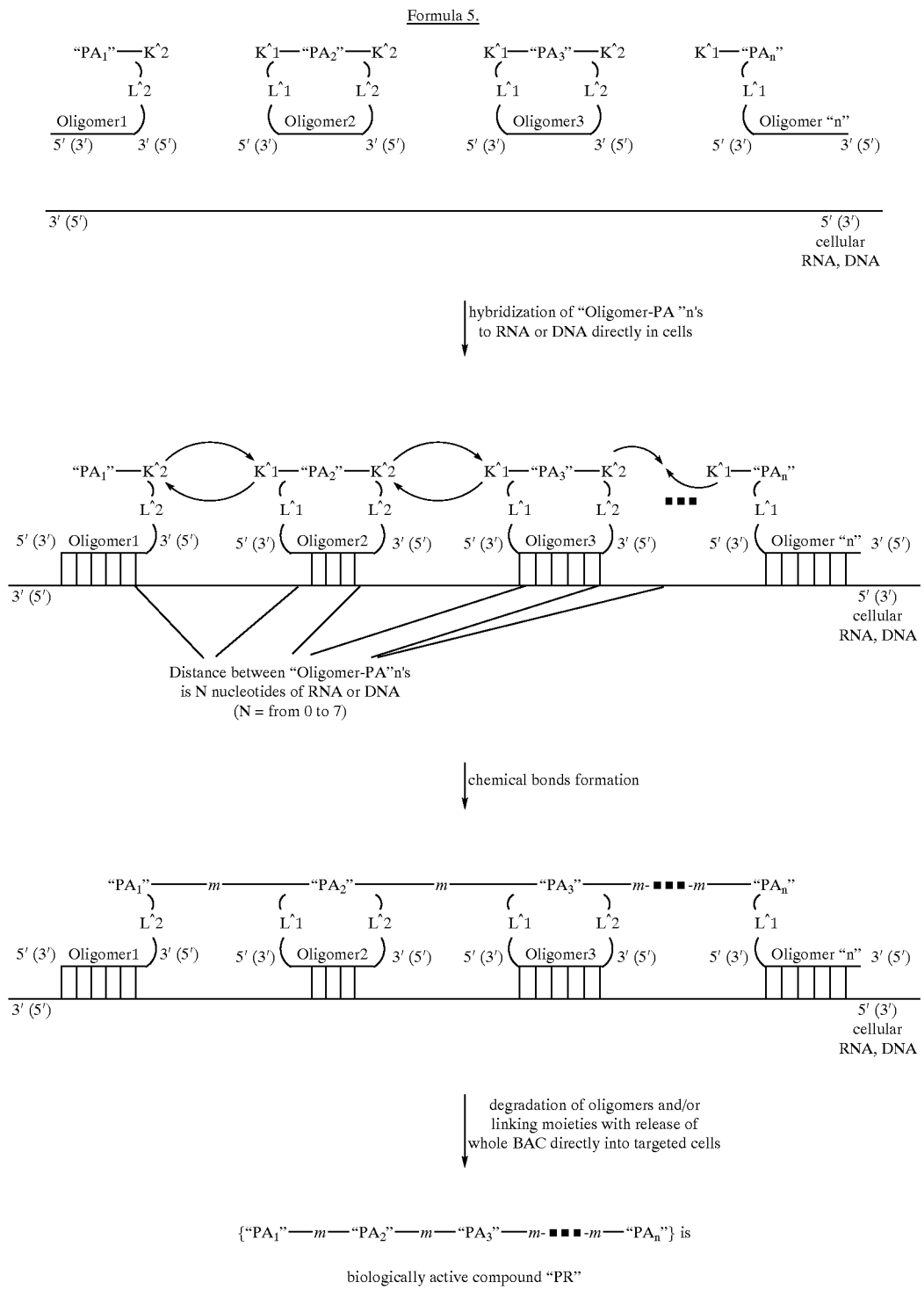

Formula 5.

biologically active compound "PR"

After simultaneous hybridization of "Oligomer$_{n-1}$-PA$_{n-1}$" and "Oligomer$_n$-PA$_n$" to cellular RNA or DNA, the chemically active groups K^1 and K^2 interact with each other to form the chemical moiety "m" between "Oligomer$_{n-1}$-PA$_{n-1}$" and "Oligomer$_n$-PA$_n$" correspondingly; This step is repeated in the cells n-1 times and combines n-1 times all {"PA"$_1$-m-"PA"$_2$-m-"PA"$_3$-m-"PA"$_4$-m- . . . -m-"PA$_{n-3}$"-m-"PA$_{n-2}$"-m-"PA$_{n-1}$"-m-"PA$_n$"} is biologically active compound "PR". The degradation of the oligomers and/or linking moieties L^1 and L^2 leads to the release of the synthesized BAC "PR" directly into targeted cells of living organism. Here, n is selected from 2 to 2000;

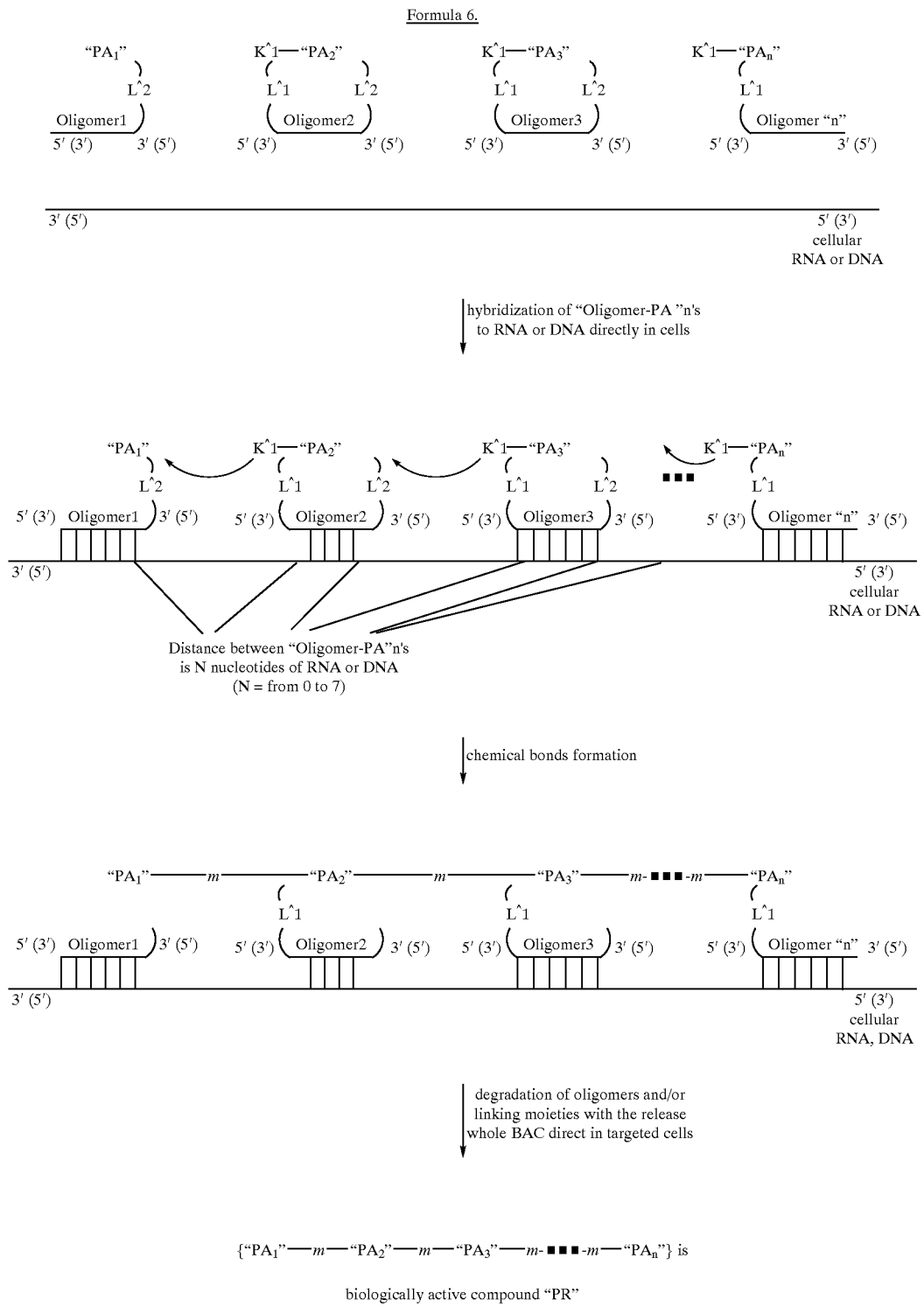

Formula 6.

After simultaneous hybridization of "oligomer$_{n-1}$-PA$_{n-1}$" and "oligomer$_n$-PA$_n$" to cellular RNA, DNA or dsDNA, the chemically active group K^1 of "oligomer$_n$-PA$_n$" interacts with the linking moiety L^2 of "oligomer$_{n-1}$-PA$_{n-1}$" to bind PA$_{n-1}$ and PA$_n$ through chemical moiety "m". This step is repeated in the cells n-1 times and combines n-1 times all PA$_n$s after hybridization of all n "oligomer-PA$_n$"s into one active molecule of the biologically active compound "PR", which consists of n PAs so that compound {PA$_1$-m-PA$_2$-m-PA$_3$-m-PA$_4$-m- . . . -m-PA$_{n-3}$-m-PA$_{n-2}$-m-PA$_{n-1}$-m-PA$_n$} is equal to the biologically active compound PR. The degradation of the oligomers and/or linking moieties L^1 by cellular enzymes or hydrolysis leads to the release of the synthesized BAC PR directly into targeted cells of living organism, here n is selected from to 2000;

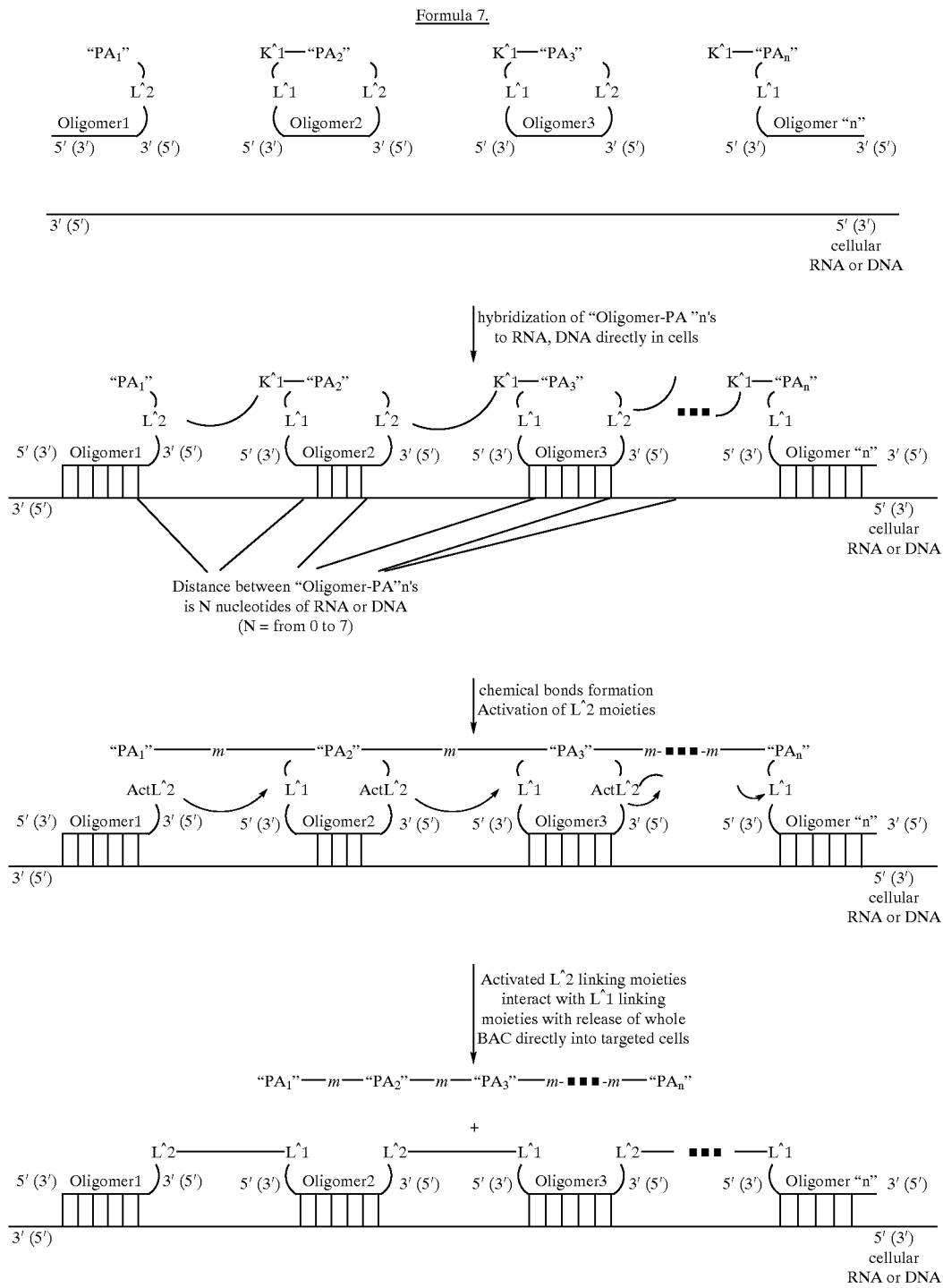

Formula 7.

After simultaneous hybridization of "Oligomer$_{n-1}$-PA$_{n-1}$" and "oligomer$_n$-PA$_n$" to cellular RNA, DNA or dsDNA, the chemically active group K^1 of "oligomer$_{n-1}$-PA$_{n-1}$" interacts with the linking moiety L^2 of "oligomer$_n$-PA$_n$" to bind PA$_{n-1}$ and PA$_n$ through chemical moiety "m". After interaction of K^1 with L^2, L^2 is chemically activated so that it can interact with linking moiety L^1 of the oligomer-PA$_{n-1}$, thus destroying the binding of the oligomer$_{n-1}$ to PA$_{n-1}$. This process is repeated n-1 times, so that only whole BAC "PR" comprising from n PA$_n$s {PA$_1$-m-PA$_2$-m-PA$_3$-m-PA$_4$-m- . . . -m-PA$_{n-3}$-m-PA$_{n-2}$-m-PA$_{n-1}$-m-PA$_n$} is released directly into the targeted cells of living organisms, here n is selected from 2 to 2000.

The chemical moieties in the Formulas 1,2,3,4,5,6 and 7 are as follows:

m is selected independently from: —S—S—, —N(H)C(O)—, —C(O)N(H)—, —C(S)—O—, —C(S)—S—, —O—, —N=N—, —C(S)—, —C(O)—O—, —NH—, —S—;

$K^1$ is selected independently from: —NH(2), dbdNH, —OH, —SH, —F, —Cl, —Br, —I, —$R^1$-C(X)—$X^1$-$R^2$;

$K^2$ is selected independently from: —NH(2), -dbd-NH, —OH, —SH, —$R^1$-C(X)—$X^1$-$R^2$, —F, —Cl, —Br, —I;

$L^1$ is independently: chemical bond, —$R^1$-, —$R^1$-O—S—$R$-$^2$-, —$R^1$-S—O—$R$-$^2$-, —$R^1$-S—S—$R^2$-, —$R^1$S—N(H)—$R^2$-, —$R^1$-N(H)—S—$R^2$-, —$R^1$-O—N(H)—$R^2$-, —$R^1$-N(H)—O—$R^2$-, —$R^1$-C(X)—X—$R^2$-;

$L^2$ is independently: chemical bond, —$R^1$, —$R^1$-O—S—$R^2$-, —$R^1$-S—O—$R^2$-, —$R^1$-S—S—$R^2$-, —$R^1$-S—N(H)—$R^2$-, —$R^1$-N(H)—S—$R^2$-, —$R^1$-O—N(H)—$R^2$-, —$R^1$-N(H)—O—$R^2$-, —$R^1$-C(X)—$X^1$-$R^2$-, —$R^1$-X—C(X)—X—C(X)—X—$R^2$-;

R-$^1$ is independently: chemical bond, alkyl, alkenyl, alkynyl, aryl, heteroalkyl, heteroalkenyl, heteroalkynyl, heteroaryl, cycloheteroaryl, carbocyclic, heterocyclic ring, $X^1$-P(X)(X)—$X^1$, —S(O)—, —S(O)(O)—, —$X^1$-S(X)(X)—$X^1$-, —C(O)—, —N(H)—, —N=N—, —$X^1$P(X)(X)—$X^1$-, —$X^1$-P(X)(X)—$X^1$, —$X^1$-P(X)(X)—$X^1$-P(X)(X)—$X^1$-P(X)(X)—$X^1$, —C(S)—, any suitable linking group;

$R^2$ is independently chemical bond, alkyl, alkenyl, alkynyl, aryl, heteroalkyl, heteroalkenyl, heteroalkynyl, heteroaryl, cycloheteroaryl, carbocyclic, heterocyclic ring, $X^1$-P(X)(X)—$X^1$, —S(O)—, —S(O)(O)—, —$X^1$-S(X)(X)—X-$^1$-, —C(O)—, —N(H)—, —N=N—, —$X^1$-P(X)(X)—$X^1$-, —$X^1$-P(X)(X)—$X^1$-P(X)(X)—$X^1$, —$X^1$-P(X)(X)—$X^1$-P(X)(X)—$X^1$, —C(S)—, any suitable linking group;

X is independently S, O, NH, Se, alkyl, alkenyl, alkynyl;

$X^1$ is independently S, O, NH, Se, alkyl, alkenyl, alkynyl.

In Formulas 1,2,3,4,5,6 and 7 the linking moieties $L^1$ and $L^2$ are bound to the first and/or last mononucleomers of the oligomers at their sugar or phosphate moiety, or directly to base, or to sugar moiety analogues, or to phosphate moiety analogues, or to base analogues.

All the described schemes demonstrate that BACs can not be synthesized in non-targeted cells because the molar concentration of the chemically active groups is too low, and without hybridization of the oligomer-PBACs to the template, specific reactions can not occur. After hybridization of the oligomer-PBACs to a specific template, the concentration of the chemically active groups is sufficient for the chemical reaction between the chemical groups of PBACs to occur. The reaction leads to chemical bond formation between PBACs and subsequent formation of a whole BAC. The degradation of the oligomers and/or linking moieties of the oligomers with PBACs leads to the release of BACS directly into targeted cells. To synthesise directly in cellsbiologically active polymers such as proteins and RNAs of determined structure more than two PBACs are used. PBACs for synthesis of proteins or RNAs are designated as $PA_n$. $PA_n$ are peptides or oligoribonucleotides. The mechanisms of the interaction of such PBACs are the same as in the synthesis of small biologically active compounds. The difference is that the PBACs (with the exception of the first and last PBACs) are bound simultaneously to the 5' and 3' ends of the oligomers so that the direction of synthesis of the biologically active protein or RNA can be determined.

Possible functions of BACs synthesized by proposed methods are: 1) Killing of cells, 2) Stimulation of the metabolism of cells 3) Blocking of important ion channels such as $Na^+$, $K^+$, $Ca^{++}$ and other ion channels, in order to inhibit signal transmissions. BACs can be proteins, peptides, alkaloids, synthetic organic compounds. They can be cleaved into two or more precursors called PBACs. After interaction between the chemical groups of PBACs, whole BAC is formed through the moiety "m".

a) In Formula 1,2,3 and 4 PBACs are designated as "A" and

A-m-B is equal to a whole BAC "T"

"m" is selected independently from —S—S—, —O—, —NH—C(O)—, —C(O)—NH—, —C(O)—, —NH—, dbdN—, —C(O)O—, —C(O)S—, —S—, —C(S)S—, —C(S)O—, —N=N—.

A-O—B is equal to a whole BAC "T"

A-NH—C(O)—B is equal to a whole BAC "T"

A-C(O)—NH—B is equal to a whole BAC "T"

A-C(O)—B is equal to a whole BAC "T"

A-NH—B is equal to a whole BAC "T"

A-dbdN—B is equal to a whole BAC "T"

A-C(O)O—B is equal to a whole BAC "T"

A-C(O)S—B is equal to a whole BAC "T"

A-C(S)S—B is equal to a whole BAC "T"

A-S—S—B is equal to a whole BAC "T"

A-C(S)O—B is equal to a whole BAC "T"

A-N=N—B is equal to a whole BAC "T"

b) A biologically active compound can be formed through the moieties "m" and "m^1". "m" and "m^1" are selected independently from: —S—S—, —O—, —NH—C(O)—, —C(O)—NH—, —C(O)—, —NH—, dbdN—, —C(O)O—, —C(O)S—, —S—, —C(S)S—, —C(S)O—, —N=N—, so that $$A \underset{m^1}{\overset{m}{\diamond}} B$$

is equal to biologically active compound "T"

This kind of interaction is represented in FIG. 4.

c) In Formulas 5, 6 and 7, precursors of BACs (PBACS) are designated as "$PA_n$", where n is selected from 2 to 2000. "PA" are peptides or oligoribonucleotides consisting of from 2 to 100 amino acids. n is the ordinal number of PA in a series of PAs and designates the sequence of binding of PAs to each other.

{"$PA_1$"-m-"$PA_2$"-m-"$PA_3$"-m- . . . -m-"$PA_{n-3}$"-m-"$PA_{n-2}$"-m-"$PA_{n-1}$"-m-"$PA_n$"} is equal to BAC "PR". BACs "PR" in this case are proteins or RNAs. Proteins can be cellular proteins, enzymes, transcription factors, ligands, signalling proteins, transmembrane proteins, cytolitical toxins, cytoplasmic and nuclear proteins and the like. RNAs are selected from mRNA, rsRNA and the like.

Toxin Daphnoretin is cleaved into two precursors. After simultaneous hybridization to cellular RNA of the oligomers bound to the daphoretin's precursors, the chemically active hydroxyl group of daphnoretin's precursor "A" interacts with the chemically active Cl group of precursor "B" to form a chemical bond between the two daphnoretin precursors. The degradation of the linking moieties and/or oligomers leads to the release of the biologically active molecule directly into targeted cells.

Figure 1:
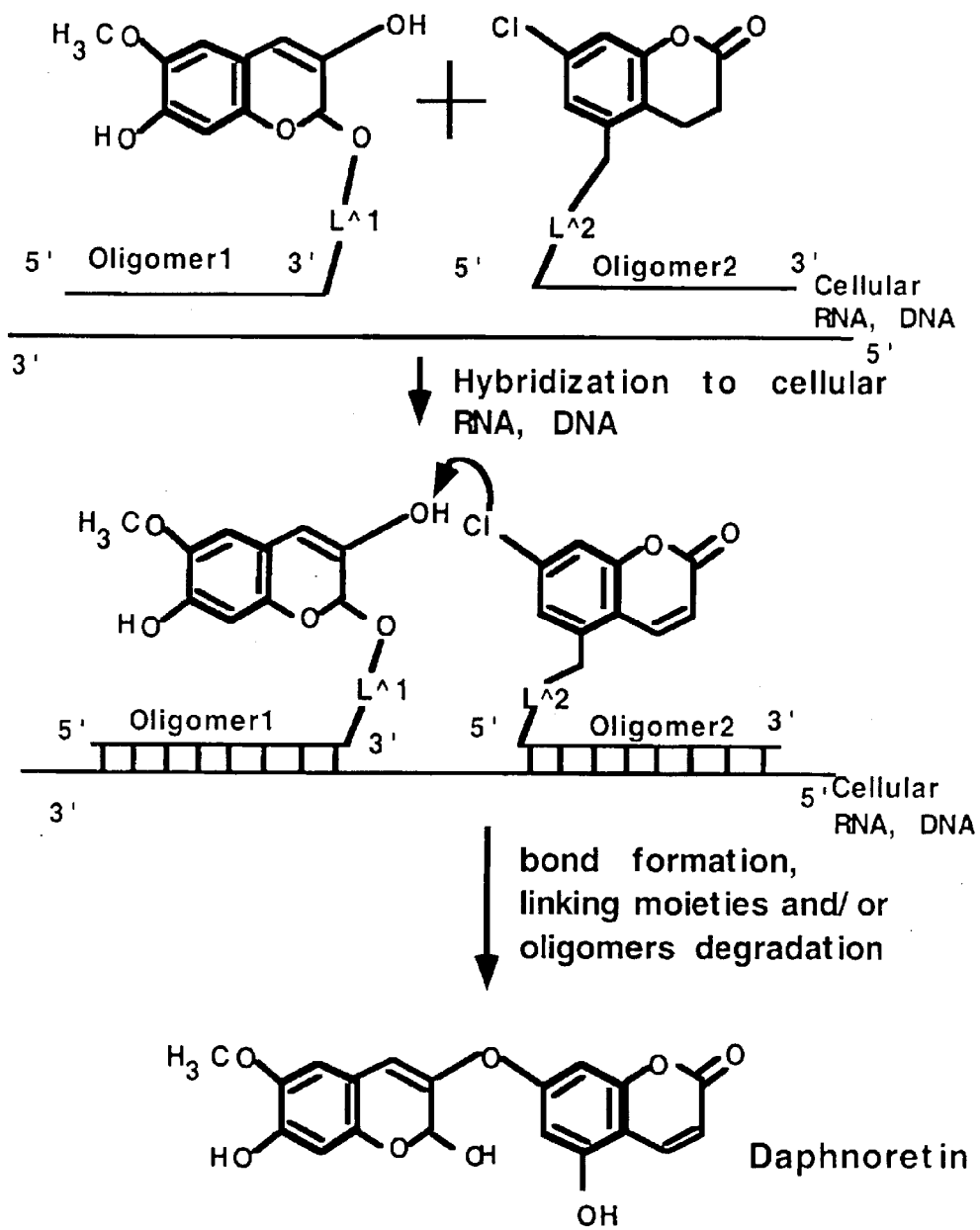
FIG. 1 Synthesis of the Toxin Daphnoretin
Figure 2:
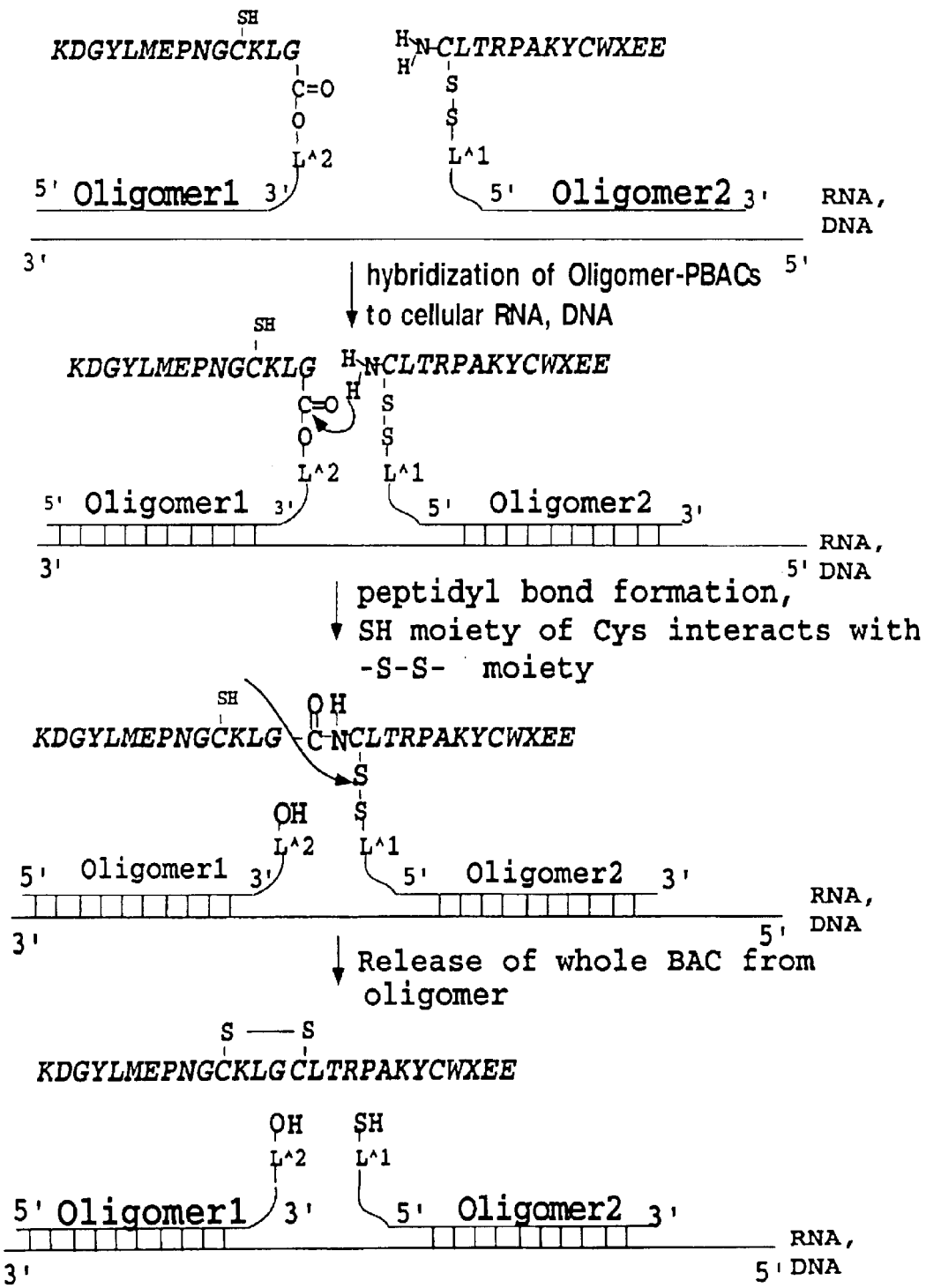

FIG. 2 Synthesis of the Neurotoxin Peptide

Neurotoxin is cleaved into two shorter, biologically inactive peptides. After hybridization to cellular RNA or DNA, the chemically active $NH_2$ group of peptide "A" interacts with the linking moiety —C(O)—O-L^2, forming a peptidyl bond. After the peptidyl bonds formation, the chemically active group —SH of peptide "B" interacts with the linking moiety L^1-S—S— which binds peptide "A" with oligomer "A". After this interaction, an —S—S— bound between the two cysteins is formed and the biologically active neurotoxin is released into targeted cells. Aminoacids are designated as italicised letters in one letter code.

Figure 3:
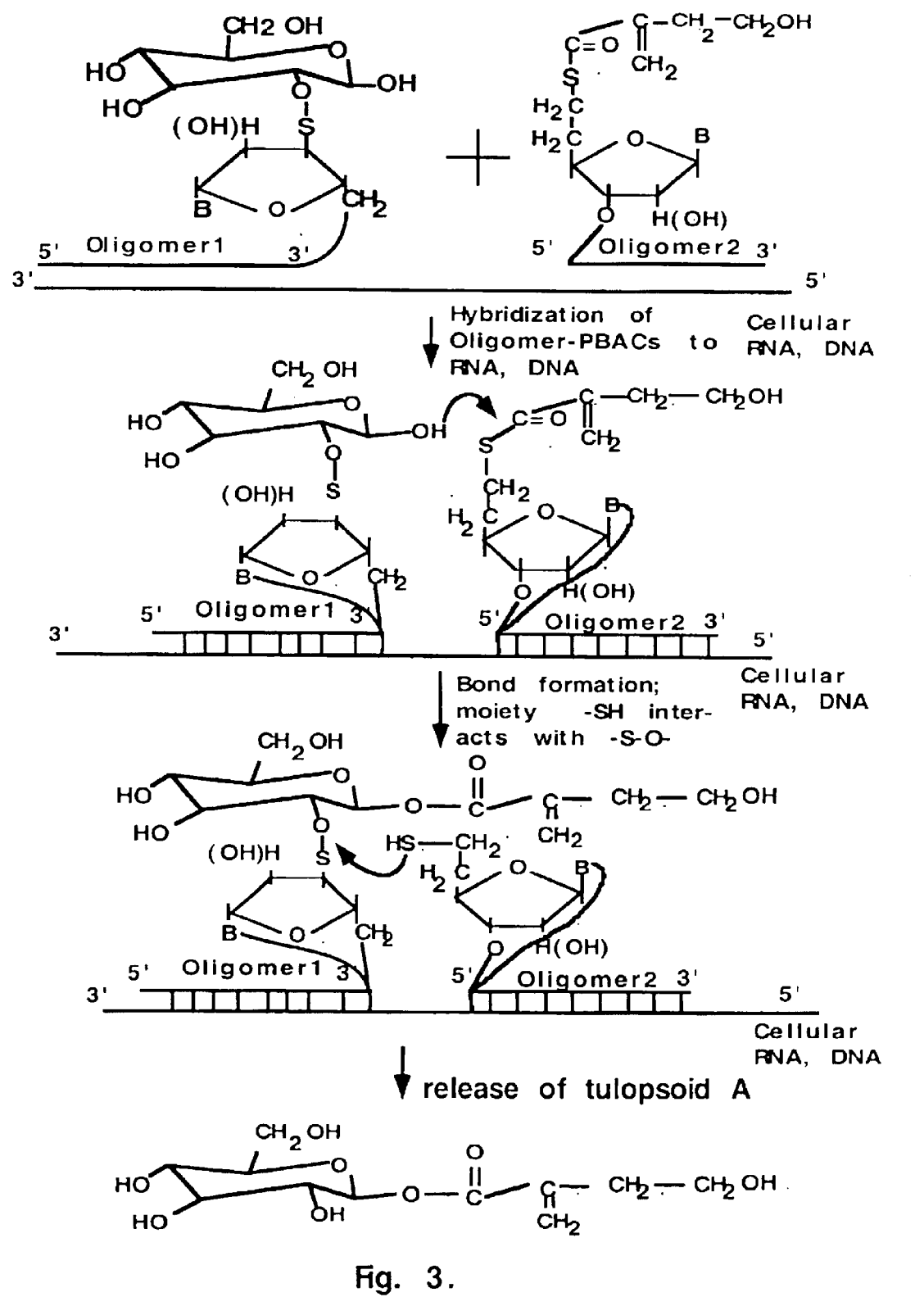

FIG. 3 The Synthesis of the Toxin Tulopsoid A

Toxin tulopsoid A is cleaved into two precursors. After simultaneous hybridization to cellular RNA of the oligomers bound to the tulopsoid A precursors chemically active hydroxyl group of the oligomer-PBAC "A" interacts with the —$CH_2$—S—C(O)— linking moiety to form a chemical bond with tulopsoid's precursor "B", releasing precursor "B" from oligomer 2. The activated —$CH_2$—SH moiety interacts with the linking moiety —S—O—, releasing the whole tulopsoid A from oligomer 1.

FIG. 4 Synthesis of the Toxin Amanitin

Toxin-amanitin is a strong inhibitor of transcription. It can be cleaved into two inactive precursors which can be used to synthesise the whole molecule of amanitin. After hybridization of all oligomers bound with the amanitin's precursors to cellular RNA or DNA, free amino group of amanitin's precursor "A" can interact with the carboxyl group —C(O)—S-L^2 to form a peptidyl bond and to release amanitin's precursor "B" from oligomer 2. The linking moiety of amanitin's precursor "A" to the oligomer 1 is semistabile. The release of precursor "A" from the oligomer 1 is performed due to action of the activated —SH group on the linking moiety —C(O)—O—S-L^1. Oligomers 3 and 4 bound with the amanitin's precursors "A" and "B" are hybridized on the same molecule of RNA or DNA. The amino group of amanitin's precursor "B" interacts with the carboxyl group —C(O)—S-L^1 to form a peptidyl bond, releasing amanitin's precursor "A" from the oligomer 3. The linking moiety of amanitin's precursor "B" to the oligomer 4 is semistabile. The release of precursor "B" from the oligomer 4 is performed due to action of the activated —SH group on the linking moiety —C(O)—O—S-L^2.

Figure 5:
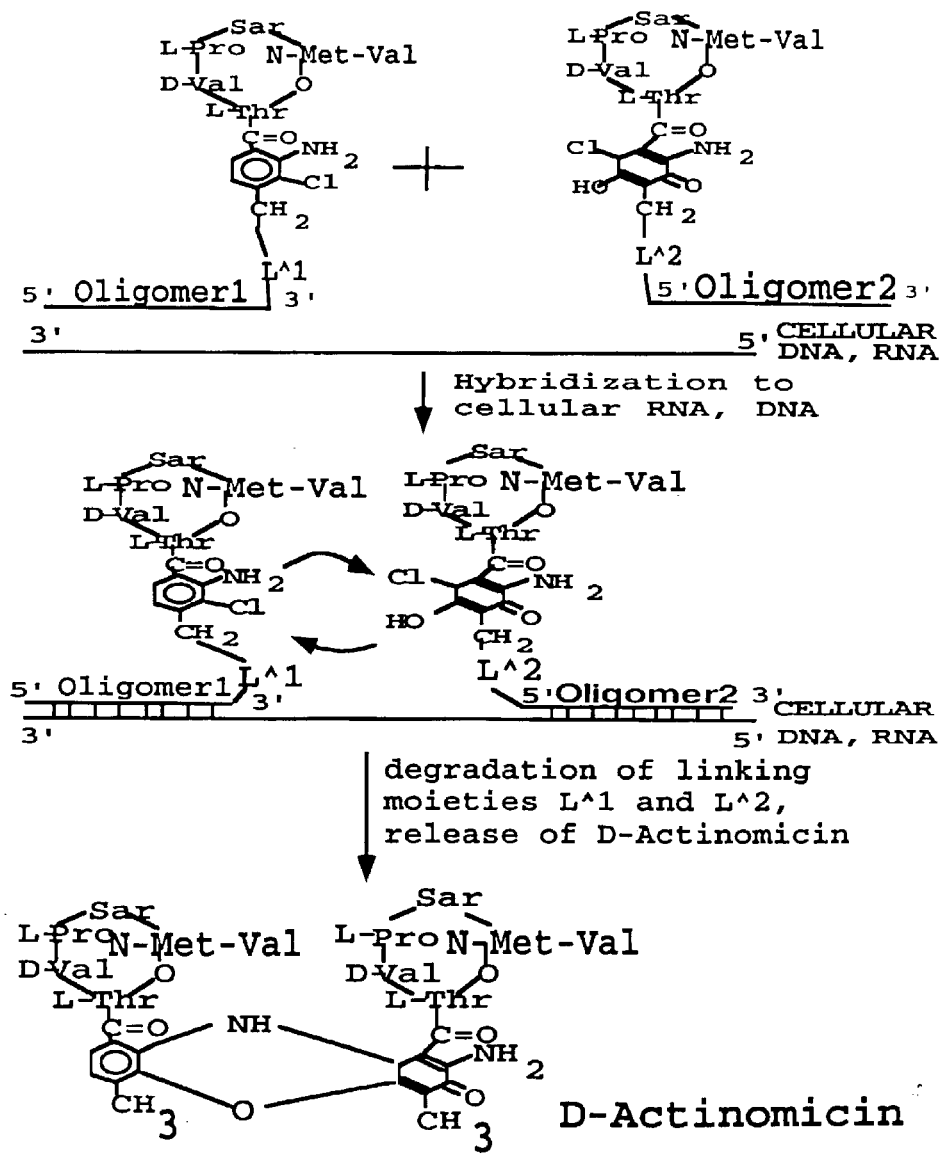

FIG. 5 Synthesis of the Toxin D-actinomicin

Toxin D-actinomicin is cleaved into two precursors. After simultaneous hybridization of two oligomer-PBACs to cellular RNA or DNA chemically active amino and halogen groups of precursor "A" interact with the chemically active halogen and hydroxyl groups of D-actinomicin's precursor "B" respectively to form two chemical bonds between the precursors.

Figure 6:
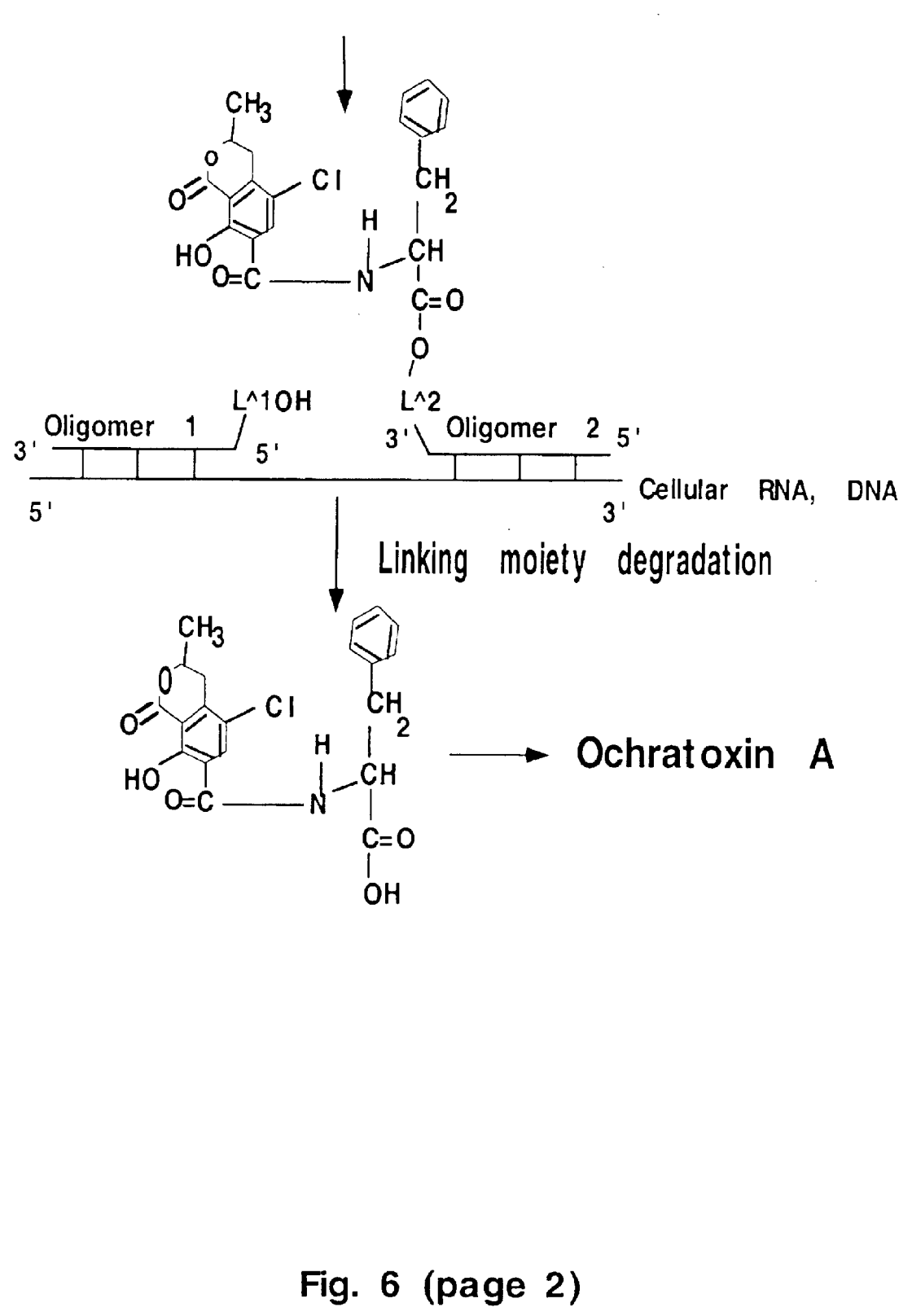

FIG. 6 Synthesis of the Toxin Ochratoxin A

Toxin ochratoxin A is cleaved into two precursors which are bound to oligomers. After simultaneous hybridization of the oligomer-PBACs to cellular RNA or DNA, the chemically active amino group of precursor "B" interacts with the moiety C(O)—O— which links precursor "A" with oligomer A, to form a chemical bond between the two ochratoxin precursors. After oligomer or linking moiety degradation in the cells the whole biologically active molecule of Ochratoxin A is released into the targeted cells.

FIG. 7 Synthesis of the Toxin Ergotamin

Toxin ergotamin is cleaved into two precursors which are bound to oligomers. After hybridization of the oligomer-PBACs to cellular RNA or DNA, the chemically active amino group of precursor "B" interacts with the moiety C(O)—O— which binds precursor "A" with oligomer "A", to form a chemical bond between the two ergotamin precursors. After degradation of the oligomers, RNA, or DNA in the cells, the whole biologically active molecule of ergotamin is released into the targeted cells.

Figure 8:
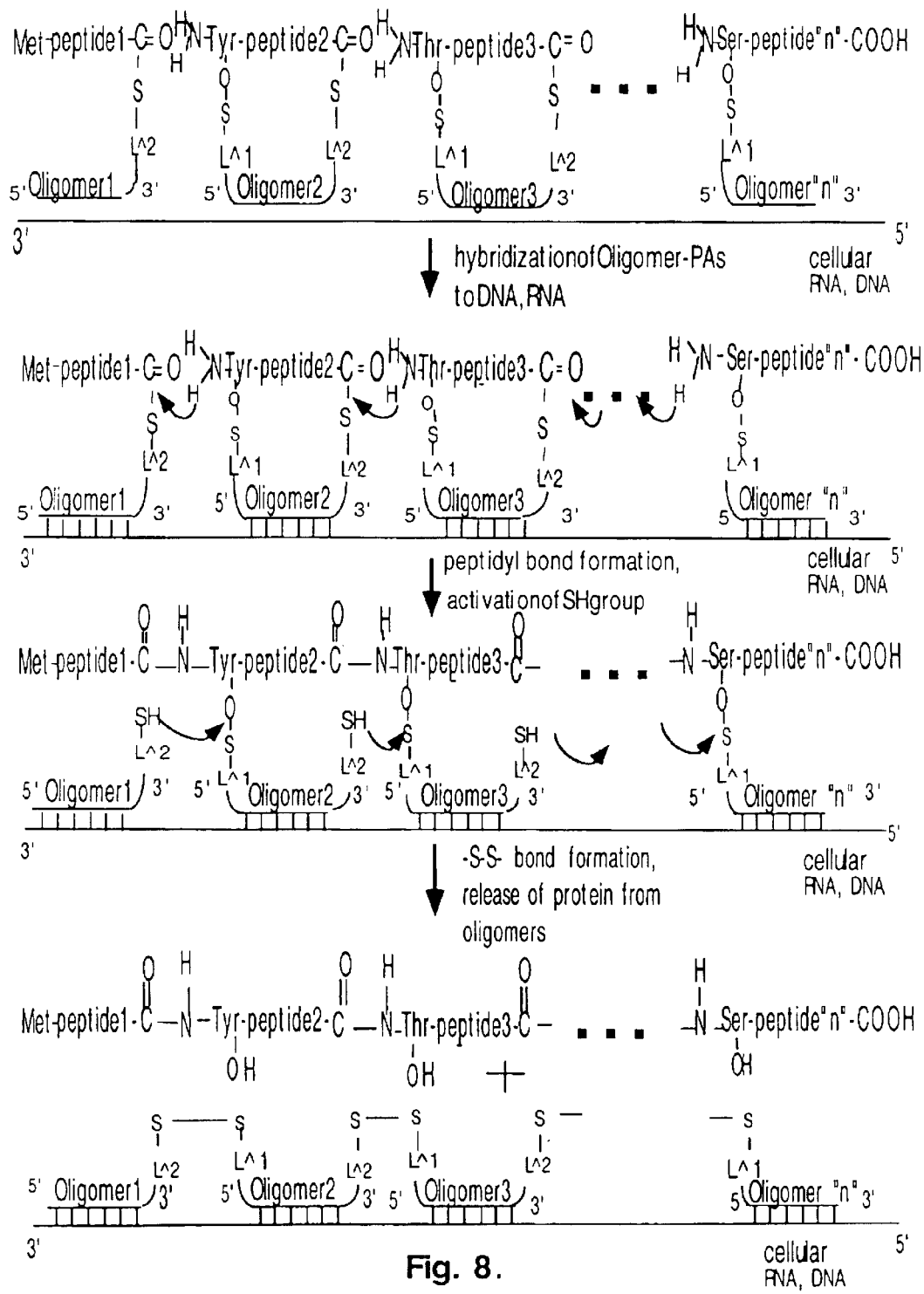

FIG. 8. Synthesis of Proteins

The synthesis of a biologically active protein of n peptides.

Peptides are bound to oligomers simultaneously at their amino and carboxy ends, with the exception of the first peptide which is bound to the oligomer at its carboxy end, and the last peptide which is bound to the oligomer at its amino terminus. Two oligomers bound to peptides (oligomer-PAs) are hybridized simultaneously to specific RNA or DNA molecules, the distance from each other between 0 and 10 nucleotides of cellular RNA or DNA. After hybridization, the amino group of the oligomer-$PA_n$ interacts with the -L^2-S—C(O)— linking moiety to form a peptidyl bond between peptide "$_{n-1}$" and peptide "n". The peptide$_{n-1}$ is released from the oligomer$_{n-1}$ at its carboxy terminus. The activated -L^2-SH group interacts then with the linking moieties —O—S-L^1 and —O—NH-L^1 which bind peptides$_n$ at their N-terminus with oligomers$_n$. After hybridization of all n oligomer-PAs the process is repeated n-1 times to bind all n peptides into one biologically active protein. Linking of the peptides at the N-terminus with oligomers is performed by aminoacids which have hydroxyl group such as serine, threonine and tyrosine.

Figure 9:
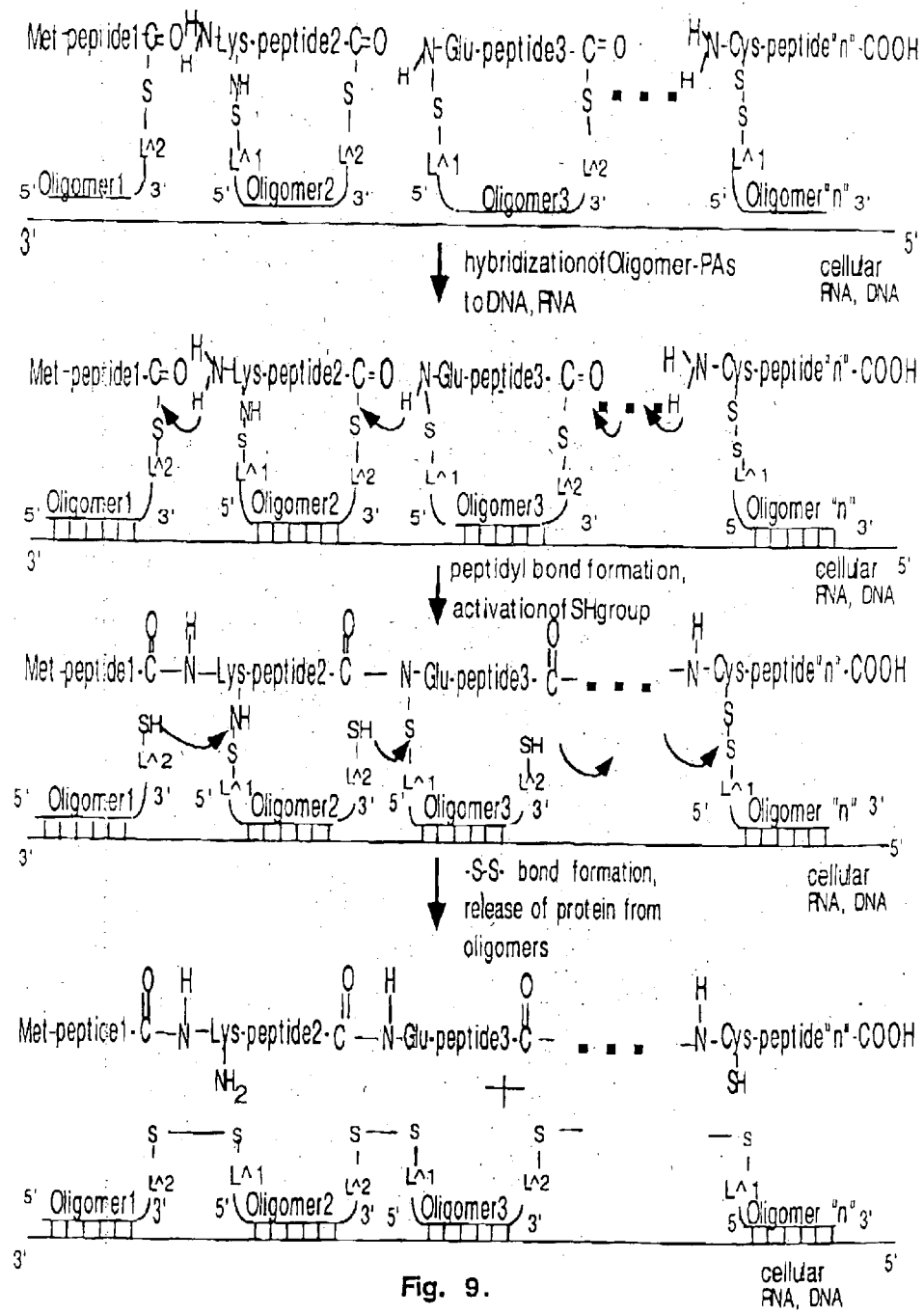

FIG. 9. Synthesis of Proteins

The same process is shown as in FIG. 8, but this time the peptides are bound at their N terminus to oligomers through aminoacids with amino and-mercapto groups, for example cysteine, arginine, asparagine, glutamine and lysine. The activated -L^2-SH group can interact with the linking groups such as —S—S-L^1, —S—NH-L^1 to form -L^2-S—S-L^1-, -L^2-S—NH-L^1 moieties and to release peptides from oligomers at their N terminus.

FIG. 10. Synthesis of RNA

In this figure "$PA_n$" are oligoribonucleotides comprising from 3 to 300 nucleotides.

n in "$PA_n$" means the ordinal number in a series of oligoribonucleotides used in the synthesis of whole RNA, where n is selected from 2 to 1000.

$PA_1$ couples with $PA_2$ through the chemical moiety —O—, then in turn $PA_1$-m-$PA_2$ couples with $PA_3$ through chemical moiety —O—, then $PA_1$-m-$PA_2$-m-$PA_3$ couples with $PA_4$ through chemical moiety —O— and so on until the last "n"th oligoribonucleotide is bound, forming the whole biologically active RNA.

The chemical moieties in FIGS. from 1 to 10 are as follows:

m is selected independently from: —S—S—, —N(H)C(O)—, —C(O)N(H)—, —C(S)—O—, —C(S)—S—, —O—, —N=N—, —C(S)—, —C(O)—O—, —NH—, —S—;

K^1 is selected independently from: —NH(2), dbdNH, —OH, —SH, —S, —Cl, —Br, —I, —R^1-C(X)—X^1-R^2;

K^2 is selected independently from: —NH(2), -dbd—NH, —OH, —SH, —R^1-C(X)—X^1-R^2, —F, —Cl, —Br, —I;

L^1 is independently: chemical bond, —R^1-, —R^1-O—S—R^2-, —R^1-S—O—R^2-, —R^1-S—S—R^2-, —R^1-S—N(H)—R^2-, —R^1-N(H)—S—R^2-,
—R^1-O—N(H)—R^2-, —R^1-N(H)—O—R^2-,
—R^1-C(X)—X—R^2-;

L^2 is independently: chemical bond, —R^1-, —R^1-O—S—R^2-, —R^1-S—O—R^2-, —R^1-S—S—R^2-, —R^1-S—N(H)—R^2-, —R^1-N(H)—S—R^2-, -R^1-O—N(H)—R^2-, —R^1-N(H)—O—R^2-, —R^1-C(X)—X^1-R^2-, —R^1-X—C(X)—X—C(X)—X—R^2-;

R^1 is independently: chemical bond, alkyl, alkenyl, alkynyl, aryl, heteroalkyl, heteroalkenyl, heteroalkynyl, heteroaryl, cycloheteroaryl, carbocyclic, heterocyclic ring, X^1-P(X)(X)—X^1, —S(O)—, —S(O)(O)—, —X^1-S(X)(X)—X^1-, —C(O)—, —N(H)—, —N=N—, —X^1-P(X)(X)—X^1-, —X^1-P(X)(X)—X^1-P(X)(X)—X^1, —X^1-P(X)(X)—X^1-P(X)(X)—X^1-P(X)(X)—X^1, —C(S)—, any suitable linking group;

R^2 is independently chemical bond, alkyl, alkenyl, alkynyl, aryl, heteroalkyl, heteroalkenyl, heteroalkynyl, heteroaryl, cycloheteroaryl, carbocyclic, heterocyclic ring, X^1-P(X)(X)—X^1, —S(O)—, —S(O)(O)—, —X^1-S(X)(X)—X^1-, —C(O)—, —N(H)—, —N=N—, —X^1-P(X)(X)—X^1-, —X^1-P(X)(X)—X^1-P(X)(X)—X^1, —X^1-P(X)(X)—X^1-P(X)(X)—X^1-P(X)(X)—X^1, —C(S)—, any suitable linking group;

X is independently S, O, NH, Se, alkyl, alkenyl, alkynyl;

X^1 is independently S, O, NH, Se, alkyl, alkenyl, alkynyl.

BEST MODE FOR CARRYING OUT THE INVENTION

The Synthesis of Different Toxins and Alkaloids Directly Into Targeted Cells

EXAMPLE 1

The Synthesis of the Toxin Alpha Amanitin

The amanitin is a toxin present in mushrooms. It acts as a very strong inhibitor of transcription in eucaryotic cells, and is therefore very strong toxin.

The synthesis of alpha-amanitin is represented in FIG. 1 The structure of the toxin is a cyclic peptide with modified amino acids. The molecule of alpha-amanitin can be cleaved into two inactive precursors, which are bound to 4 oligomers through linking moieties L^1 and L^2, designated in FIG. 1. After hybridization of all oligomers to the same molecule of RNA the synthesis of toxin amanitin is occured.

EXAMPLE 2

The Synthesis of Biologically Active Peptides

The synthesis of BACs consisting of amino acids makes possible the synthesis of practically any peptide. These peptides can be involved in a wide variety of processes. The specific synthesis will occur only in the cells where the specific sequences are represented.

The synthesis of peptides such as endorphins or toxins which block Na, K, Ca channels can be performed directly on specific RNA or DNA sequences. These peptides can act as agents stimulating cells of the nervous system, or as analgesic agents. To date, the number of known biologically active peptides is enormous. The peptides can be synthesized from natural aminoacids as well as from synthetic amino acids of D or L conformations.

The synthesis of neurotoxin is represented in FIG. 2.

EXAMPLE 3

The Synthesis of the Toxin Tulopsoid A

Toxin tulopsoid A is an alkaloid and is a strong cytolitical toxin.

Toxin tulopsoid A is cleaved into two precursors. The chemically active hydroxyl group of precursor "A" can interact after hybridization with the —$CH_2$—S—C(O)— moiety to form a chemical bond with tulopsoid's precursor "B", with the release of precursor "B" from the oligomer. The activated —$CH_2$—SH moiety interacts with the linking moiety —S—O—, releasing the whole tulopsoid from oligomer (FIG. 3).

EXAMPLE 4

The Synthesis of the Toxin Daphnoretin

Toxin daphnoretin is an alkaloid and is a strong cytolitical toxin.

Toxin Daphnoretin is cleaved into two precursors. After simultaneous hybridization of the oligomers coupled to the daphnoretin's precursors the chemically active hydroxyl group of daphnoretin's precursor "A" interacts with the chemically active Cl group of precursor "B" to form chemically bond between daphnoretin's precursors. The degradation of the oligomers or linking groups leads to the release of the biologically active molecule directly into targeted cells (FIG. 4).

EXAMPLE 5

The Synthesis of the Toxin D-actinomicin

Toxin D-actinomicin is an alkaloid and is a strong cytolitical toxin.

Toxin D-actinomicin is cleaved into two precursors. After hybridization of two oligomers to cellular RNA or DNA, the chemically active groups amino and halogen of precursor "A" interact with the chemically active groups halogen and hydroxyl respectively of D-actinomicin's precursor "B" to form two chemical bonds between the precursors (FIG. 5.).

EXAMPLE 6

The Synthesis of the Toxin Ochratoxin A

Toxin ochratoxin A is an alkaloid and is a strong cytolitical toxin.

Toxin ochratoxin A is cleaved into two precursors bound to oligomers. After hybridization of the oligomers to cellular RNA or DNA, the chemically active amino group of the precursor "B" interacts with the moiety —O—C(O) of precursor "A" to form a chemical bond between the two ochratoxin precursors. After the degradation of the oligomers or linking moieties in the cells, whole, biologically active molecules of Ochratoxin A will be released into targeted cells (FIG. 6.).

EXAMPLE 7

The Synthesis of the Toxin Ergotamin

Toxin ergotamin is an alkaloid and is a strong cytolitical toxin.

Toxin ergotamin is cleaved into two precursors which are bound to oligomers. After hybridization of the oligomers to cellular RNA or DNA, the chemically active amino group of precursor "B" interacts with moiety —O—C(O) of precursor "A" to form a chemical bond between the two ergotamin precursors. After degradation of the oligomers or linking moieties in the cells, whole, biologically active molecules of ergotamin will be released into the targeted cells.

By using more than two oligonucleotides bound at their 5',3' ends to precursors of biologically active compounds, higher concentration level of the biologically active substances can be achieved into targeted cells.

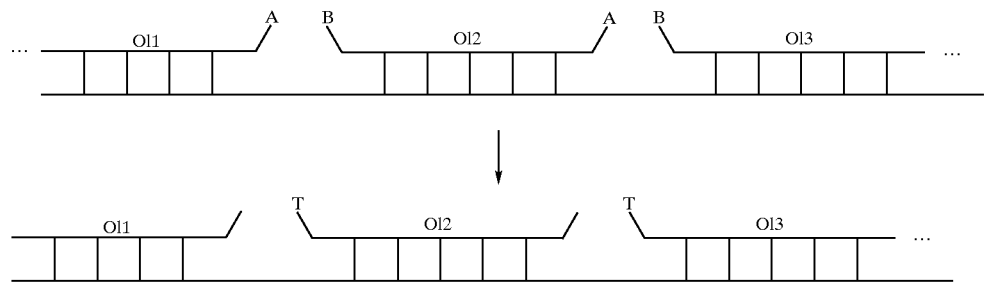

O11, O12, O13 are oligomers 1,2,3 which at their 3' and 5' ends are bound to precursors of biologically active substances.

Such linking can also prevent oligonucleotides from exonuclease degradation and constabilise their activity in cells. In any case, the products of the degradation of the peptides and oligonucleotides formed from natural aminoacids and nucleotides are not toxic, and can be used by cells without elimination from the organism or toxic effects on other healthy cells.

All the toxins described can be used for the synthesis of toxins in cells infected by viruses, using the hybridization of the oligomers to double stranded DNA. In U.S. Pat. No. 5,571,937 the homopurine sequences of HIV 1 were found. One such sequence is 5'-GMGGMTAGMGMGMGGTGGAGAGAGAGA-3' (seq ID NO 43 U.S. Pat. No. 5,571,937). Using two oligomers: (A-5'-GMGGMTAGAAGMG-3') (SEQ ID No. 1) and (B-5'-MGMGGTGGAGAGAGAGA-3') (SEQ ID No. 2) bound through linking moieties L 1 and L 2 to PBACs, synthesis of the corresponding BACs directly in human cells infected by HIV1 can be achieved. The toxin will be synthesized only in thouse cells infected by HIV1. Other healthy cells will be not killed by synthesized toxin.

The Synthesis of Proteins

The synthesis of protein can be performed according to the scheme designated in Formulas 5, 6 and 7 and in FIGS. 8, 9.

Relatively small molecules can be used to synthesize the whole active proteins in any tissue of a living organism. These small molecules can easily penetrate the blood brain barrier, or enter other tissues. The degradation products of such compounds can be used as nutrients for other cells. They are also not toxic to other cells where specific RNAs are not present, in the case where oligomers are oligoribo (deoxy)nucleotides. The synthesis of whole proteins of 50 kDa can be performed on one template 300–500 nucleotides in length using oligomers of the length 10–50 nucleomonomers bound to peptides consisting of 2–30 amino acids. Only 10–20 such PBACs are necessary to synthesise a protein of molecular weight 50 kDa. Theoretically, it is possible to synthesise the proteins of any molecular mass.

The number of oligomer-PAs can vary from 1 to 1000, but the efficiency of synthesis of large proteins is very low and depends on the velocity of the reaction and the degradation of the oligomer-PAs in the living cells.

By this method, synthesized proteins can be modified later in the cells by cellular enzymes to achieve the biologically active form of the protein.

The method allows the synthesis of specific proteins only in thouse cells in which the proteins are needed. Any type of proteins can be synthesized by this method. These proteins can be involved in cellular metabolism, transcription regulation, enzymatic reactions, translation regulation, cells division or apoptosis.

The mechanism allows the synthesis of any protein directly into targeted cells. The synthesized proteins could inhibit a cell's growth or division, or could stimulate division and metabolism of cells where specific RNAs are expressed. By the method described, it is possible to synthesise not only one protein, but many different proteins in the selected cells. These proteins could change even the differentiation of the targeted cells. The targeted cells can be somatic cells of living organisms, tumour cells, cells of different tissues, bacterial cells or cells infected by viruses.

EXAMPLE 8

Synthesis of the Tumour Suppresser p53

The synthesis is performed according to Formula 6. In the example below, the peptides from $PA_2$ to $PA_{14}$ are bound at their $NH_2$ end to the linking moiety $L^{\wedge}2$ through the OH group of amino acids serine or threonine. The linking moiety $L^{\wedge}2$ is bound to the phosphate or sugar moiety of the nucleotides localised at the 5' end of the corresponding oligomers. The amino acids at the COOH ends of the peptides are bound to the oligomer through acyl moieties ($L^{\wedge}1$) bound to the 3' OH group of sugar moiety of the nucleotide localised at 3' end. After hybridization to specific cellular RNA, the $NH_2$ group of the oligomer$_n$-$PA_n$ interacts with the linking acyl group of the oligomer$_{n-1}$-$PA_{n-1}$ to form a peptidyl bond between two oligomer-PAs. The whole P53 protein can be synthesized using only 14 oligomer-PAs and a 250 nucleotide long region of RNA for hybridization to the oligomer-PAs.

$PA_1$, $PA_2$, $PA_3$, $PA_4$, $PA_5$, $PA_6$, $PA_7$, $PA_8$, $PA_9$, $PA_{10}$, $PA_{11}$, $PA_{12}$, $PA_{13}$ and $PA_{14}$ are the peptides which are bound to the oligomers. The sequences of the peptides are represented below.

$PA_1$—MEEPQSOPSV EPPLSQETFS DLWKLLPENN VL (SEQ ID No. 3)

$PA_2$—SPLPSQAH DDLMLSPDDI EQWF (SEQ ID No. 4)

$PA_3$—TEDPGPDEAP RHPEAAPRVA PAPMP (SEQ ID No. 5)

PA$_4$—TPAAPAPAPS WPLSSSVPSQ KTYQG (SEQ ID No. 6)

PA$_5$—SYGFRLGFLHS GTAKSVTCRY (SEQ ID No. 7)

PA$_6$—SPAL NKMFCQLAKT CPVQLWVDSTPPPG (SEQ ID No. 8)

PA$_7$—TRVRAM AIYKQSQHMT EVVRRCPHHE (SEQ ID No. 9)

PA$_8$—TCSDSDGLAP PQHLIRVEGN LRVEYLDDRN (SEQ ID No. 10)

PA$_9$—TFRHSVVVPY EPPEVGSDCT TIHYNYMCNS (SEQ ID No. 11)

PA$_{10}$—SCMGGMNRRP ILTIITLEDS SGNLLGRN (SEQ ID No. 12)

PA$_{11}$—SFEVRVCACPGR DRRTEEENLR KKGEPHHELPPG (SEQ ID No. 13)

PA$_{12}$—STKRALPN NTSSSPQPKK KPLDGEYF (SEQ ID No. 14)

PA$_{13}$—TLQIRGRERFEM FRELNEALEL KDAQAGKEPGG (SEQ ID No. 15)

PA$_{14}$—SRAHSSHLK SKKGQSTSRH KKLMFKTEGP DSD (SEQ ID No. 16)

Aminoacids are designated in bold/italicised one letter code.
A—alanine, R—arginine, N—asparagine, D—aspartic acid, C—cysteine, Q—glutamine, E—glutamic acids, G—glycine, H—histidine, I—isoleucine, L—leucine, K—lysine, M—methionine, F—phenylalanine, P—proline, S—serine, T—threonine, W—tryptophan, Y—tyrosine, V—valine.

The tyrosine in PA$_7$ can be chemically phosphorylated. In this way an already active form of the protein can be synthesized directly in the cells. It is possible to include any modification at any amino acid of the PAs.

```
oligomer 1  5'-cccaatccctcttgcaactga-3'   (SEQ ID NO. 17)
oligomer 2  5'-attctactacaagtctgccctt-3'  (SEQ ID NO. 18)
oligomer 3  5'-ttgtgaccggctccactg-3'     (SEQ ID NO. 19)
oligomer 4  5'-taccttggtacttctctaa-33'   (SEQ ID NO. 20)
oligomer 5  5'-atgccatattagcccatcaga-33' (SEQ ID NO. 21)
oligomer 6  5'-ccaagcattctgtccctcctttt-3' (SEQ ID NO. 22)
oligomer 7  5'-tccggtccggagcacca-3'      (SEQ ID NO. 23)
oligomer 8  5'-gccatgacctgtatgttaca-3'   (SEQ ID NO. 24)
oligomer 9  5'-ggtgtgggaaagttagcggg-3'   (SEQ ID NO. 25)
oligomer 10 5'-gcgaattccaaatgattttaa-33' (SEQ ID NO. 26)
oligomer 11 5'-aatgtgaacatgaataa-33'     (SEQ ID NO. 27)
oligomer 12 5'-agagtgggatacagcatctata-3' (SEQ ID NO. 28)
oligomer 13 5'-acaaaaccattccactctgatt-3' (SEQ ID NO. 29)
oligomer 14 5'-ttggaaaaactgtgaaaaa-3'    (SEQ ID NO. 30)
```

All oligomers herein are oligonucleotides antiparallel to the human plasminogen antigen activator mRNA. After hybridization of the oligomer-PAs to the RNA, the distance between the 3' ends of the oligomer$_{n-1}$ and the 5' ends of the oligomer$_n$ is equal to 0 nucleotides of plasminogen antigen activator mRNA. n as used herein is from 1 to 14.

```
Oligomer1-PA1 is   H2N-MEEPOSDPSVEPPLSQETFSDLWKLLPENNVL   (SEQ ID No. 3)
                                                   L^1
                   5'-cccaatcoctcttgcaactga-3'         (SEQ ID No. 17)

Oligomer2-PA2 is   H2N-SPLPSOAMDDLMLSPDDIEQWF           (SEQ ID No. 4)
                    L^2                  L^1
                   5'-attctactacaagtctgccctt-3'        (SEQ ID No. 18)

Oligomer3-PA3 is   H2N-TEDPGPDEAPRMPEAAPRVAPAPMP        (SEQ ID No. 5)
                    L^2                      L^1
                   5'-ttgtgaccggctccactg-3'            (SEQ ID No. 19)

Oligomer4-PA4 is   H2N-TPAAPAPAPSWPLSSSVPSQ- KTYQG      (SEQ ID No. 6)
                     L^2                       L^1
                   5'-taccttqgtacttctctaa-3'           (SEQ ID No. 20)

Oligomer5-PA5 is   H2N-SYGFRLGFLHSGTAKSVTCTY            (SEQ ID No. 7)
                     L^2                 L^1
                   5'-atgccatattagcccatcaga-3'         (SEQ ID No. 21)

Oligomer6-PA6 is   H2N-SPALNKMFCQLAKTCPVQLWVDSTPPPG     (SEQ ID No. 8)
                     L^2                      L^1
                   5'-ccaagcattctgtccctccttt-3'        (SEQ ID No. 22)

Oligomer7-PA7 is   H2N-TRVRAMAIYKQSQHMTEVVRRCPHHE       (SEQ ID No. 9)
                     L^2                     L^1
                   5'-tccggtccggagcacca-3'             (SEQ ID No. 23)
```

-continued

| | | |
|---|---|---|
| Oligomer$_8$-PA$_8$ is | H$_2$N-TCSDSDGLAPPQHLIRVEGNLRVEYLDDRN<br>     L^2                                L^1 | (SEQ ID No. 10) |
| | 5'-gccatgacctgtatgttaca-3' | (SEQ ID No. 24) |
| Oligomer$_9$-PA$_9$ is | H$_2$N-TFRHSVVVPYEPPEVGSDCTTIHYNYMCN<br>     L^2                                L^1 | (SEQ ID No. 11) |
| | 5'-ggtgtgggaaagttagcggg-3' | (SEQ ID No. 25) |
| Oligomer$_{10}$-PA$_{10}$ is | H$_2$N-SSCMGGMNRRPILTIITLEDSSGNLLGRN<br>     L^2                                L^1 | (SEQ ID No. 12) |
| | 5'-gcgaattccaaatgattttaa-3' | (SEQ ID No. 26) |
| Oligomer$_{11}$-PA$_{11}$ is | H$_2$N-SFEVRVCACPGRDRRTEEENLRKKGEPHHELPPG<br>     L^2                                            L^1 | (SEQ ID No. 13) |
| | 5'-aatgtgaacatgaataa-3' | (SEQ ID No. 27) |
| Oligomer$_{12}$-PA$_{12}$ is | H$_2$N-STKRALPNNTSSSPQPKKKPLDGEYF<br>     L^2                           L^1 | (SEQ ID No. 14) |
| | 5'-agagtgggatacagcatctata-3' | (SEQ ID No. 28) |
| Oligomer$_{13}$-PA$_{13}$ is | H$_2$N-TLQIRGRERFEMFRELNEALELKDAQAGKEPGG<br>     L^2                                      L^1 | (SEQ ID No. 15) |
| | 5'-acaaaaccattccactctgatt-3' | (SEQ ID No. 29) |
| Oligomer$_{14}$-PA$_{14}$ is | H$_2$N-SRAHSSHLKSKKGQSTSRHKKLMFKTEGPDSD<br>     L^2 | (SEQ ID No. 16) |
| | 5'-ttggaaaaactgtgaaaaa-3' | (SEQ ID No. 30) |

The oligomer$_n$-PA$_n$ (n is selected from 1 to 14) are peptides chemically bound to oligomers which can form stable duplex structure with the plasminogen antigen activator mRNA expressed in human ovarian tumour cells. Using the plasminogen antigen activator mRNA it is possible to synthesize any other protein or small BAC. All these proteins or BACs will be synthesized only in those cells where the human plasminogen activator mRNA is expressed. In the case of the human plasminogen activator mRNA, the synthesis of the protein or BAC will occur only in ovarian tumour cells. Oligomer 1 at its 3' end is bound to the "C" end of the peptide PA$_1$ of p53 through the linking moiety L^1. Oligomers 2 to 13 are bound at their 5' and 3' ends to peptides PA$_2$ to PA$_{13}$ at their "N" and "C" ends respectively, through the linking moieties L^2 and L^1. Oligomer14 at it's 5' end is bound to the "N" end of the peptide PA$_{14}$ of p53 through the linking moiety L^2. The first methionine of PA$_1$ is formylated, and the amino end of peptide$_1$ is not bound to Oligomer$_1$. The last amino acid at the carboxyl end of PA$_{14}$ is not bound to Oligomer$_{14}$. Only 14 peptides chemically bound to 14 oligomers are required to synthesize p53 tumour suppresser specifically in the cells of the ovarian tumour. In any type of tumour cell RNAs specific to this cell type are expressed. By this method, it is possible to synthesise any protein or BACs described above on these RNAs.

The 14 Oligomer-PAs are hybridized on the mRNA in such a manner that the 3' end of the oligomer$_1$-PA$_1$ is located at a distance from the 5' end of the oligomer$_2$-PA$_2$ which is equal to 0 nucleotides of the plasminogen antigen activator mRNA. The distance between the 5' end of the Oligomer$_3$-PA$_3$ and the 3' end of the Oligomer$_2$-PA$_2$ is equal to 0 nucleotides of the plasminogen antigen activator mRNA. The distance between the 5' end of the Oligomer$_4$-PA$_4$ and the 3' end of the oligomer$_3$-PA$_3$ is equal to 0 nucleotides of the plasminogen antigen activator mRNA etc. In other words, after hybridization of the oligomer-PAs to the plasminogen antigen activator mRNA, the distance between the 3' end of the oligomer$_{n-1}$-PA$_{n-1}$ and the 5' end of the Oligomer$_n$-PA$_n$ is equal to 0 nucleotides of the plasminogen antigen activator mRNA.

After the degradation of the oligomers and/or linking moieties, the synthesized protein p53 is released into the determined cells.

{H$_2$N-PA$_1$-C(O)NH-PA$_2$-C(O)NH-PA$_3$-C(O)NH-PA$_4$-C(O)NH-PA$_5$-C(O)NH-PA$_6$--C(O)NH-PA$_7$-C(O)NH-PA$_8$-C(O)NH-PA$_9$-C(O)NH-PA$_{10}$-C(O)NH-PA$_{11}$-C(O)NH --PA$_{12}$-C(O)NH-PA$_{13}$-C(O)NH-PA$_{14}$-COOH} is biologically active protein—tumour suppresser p53. The yield of synthesis in the cells can be very low, even <1%, because the synthesis occurs directly in the targeted cells. Using different RNAs transcribed at different levels in the same cells, it is possible change the amount of the protein synthesized by this method.

The variety of proteins which can be synthesized by the proposed method is enormous. Limitations could occur if the proteins to be synthesised are very large or have many hydrophobic amino acids.

The distance between the 5' and 3' ends of the oligomer-PAs after hybridization to the template can be varied between 0 and 10 nucleotides of the target RNA.

In the example described above, the oligomers are anti-parallel to the plasminogen antigen activator mRNA. Using RNAs which expressed specifically in different tumour cells, the synthesis of any protein in these cells can be achieved. One example of such RNA is metastasin (mts-1) mRNA (Tulchinsky et al.1992, accession number g486654).

Using oligomers antiparallel to metastasin mRNA it is possible to synthesise any toxin or protein specifically in human metastatic cells.

Using different RNAs expressed specifically in different tissues or in cells infected by viruses, or in bacterial cells, it is possible to synthesise any toxin or protein specifically in these cells.

THE EXAMPLE 10

Synthesis of the tumour suppresser p53 according to Formula 7. After hybridization of the oligomer-PAs to mRNA specific to ovarian tumour cells (NbHOT Homo sapiens mRNA accession number AA402345), the chemical moiety K^1 of PA$_2$ (in this example K^1 is NH$_2$ group) interacts with the linking moiety L^2 of the oligomer$_1$-PA$_1$. After the interaction has occurred, the peptide PA$_1$ is bound through the peptidyl bond to the peptide PA$_2$ and is released from the 5' end of the oligomer$_1$. The linking moiety L^2 of the oligomer$_1$ is activated so that it interacts with the linking moiety L^1 of oligomer$_2$, and the peptide PA$_1$-C(O)NH-PA$_2$ is released from the 3' end of oligomer$_2$. The chemical moiety K^1 of oligomer$_3$-PA$_3$ interacts with the linking moiety L^2 of oligomer$_2$-{PA$_1$-C(O)NH-$PA_2$} to bind peptide $PA_3$ with $PA_1$-C(O)NH-$PA_2$, releasing peptide $PA_1$-C(O)NH-$PA_2$-C(O)NH-$PA_3$ from $oligomer_2$. The activated linking moiety L^2 of $oligomer_2$ interacts with the linking moiety L^1 and releases the peptide $PA_1$-C(O)NH-$PA_2$-C(O)NH-$PA_3$ from the 3' ends of $oligomer_3$. The processes described above are repeated in the cells 13 times. In such as manner, the protein: {$PA_1$-C(O)NH-$PA_2$-C(O)NH-$PA_3$-C(O)NH-$PA_4$-C(O)NH-$PA_5$-C(O)NH-$PA_6$-C(O)NH-$PA_7$-C(O)NH-$PA_8$-C(C)NH-$PA_9$-C(O)NH-$PA_{10}$-C(O)NH-$PA_{11}$-C(O)NH-$PA_{12}$-C(O)NH-$PA_{13}$-C(O)NH-$PA_{14}$} can be synthesized. Neither the degradation of the oligomers nor the degradation of the linking moieties is necessary to release the protein from the oligomers. Peptidyl bond formation between $Pa_{n-1}$ and $PA_n$ and degradation of the linking moieties L^2 proceed simultaneously with the release of PAs from the 5' ends of the oligomers. The activated linking moieties L^2 interact with the linking moieties L^1 to release the bound peptides from the 3' ends of the oligomers.

$PA_1$—HEEPQSDPSVEPPLSOETFSDLWKLLPENNVL (SEQ ID No. 3)

$PA_2$—SPLPSQAMDDLMLSPDDIEQWF (SEQ ID No. 4)

$PA_3$—TEDPGPDEAPRMPEAAPRVAPAPMP (SEQ ID No. 5)

$PA_4$—TPMPAPAPSWPLSSSVPSQKJYQG (SEQ ID No. 6)

$PA_5$—SYGFRLGFLHSGTAKSVTCTY (SEQ ID No. 7)

$PA_6$—SPALNKMFCQLAKTCPVQLWVDSTPPPG (SEQ ID No. 8)

$PA_7$—TRVRAMAIYKQSQHMTEVVRRCPHHE (SEQ ID No. 9)

$PA_8$—TCSDSOGLAPPQHLIRVEGNLRVEYLDDRN (SEQ ID No. 10)

$PA_9$—TFRHSVVVPYEPPEVGSDCTTIHYNYMCNS (SEQ ID No. 11)

$PA_{10}$—SCMGGMNRRPIL TIITLEDSSGNLLGRN (SEQ ID No. 12)

$PA_{11}$—SFEVRVCACPGRORRTEEENLRKKGEPHHELPPG (SEQ ID No. 13)

$PA_{12}$—TKRALPNNTSSSPQPKKKPLDGEYF (SEQ ID No. 14)

$PA_{13}$—TLQIRGRERFEMFRELNEALELKDAQAGKEPGG (SEQ ID No. 15)

$PA_{14}$—SRAHSSHLKSKKGQSTSRHKKLMFKTEGPDSD (SEQ ID No. 16)

where $PA_1$ to $PA_{14}$ are peptides bound to oligomers,

Aminoacids are designated in bold/italicised one letter code.

A—alanine, R—arginine, N—asparagine, D—aspartic acid, C—cysteine, Q—glutamine, E—glutamic acids, G—glycine, H—histidine, I—isoleucine, L—leucine, K—lysine, M—methionine, F—phenylalanine, P—proline, S—serine, T—threonine, W—tryptophan, Y—tyrosine, V—valine.

| | | |
|---|---|---|
| $Oligomer_1$ | 3' ATGGGCGGTAGGTAC 5' | (SEQ ID No. 31) |
| $Oligomer_2$ | 3' TAGCGGTGCCCTCGA 5' | (SEQ ID No. 32) |
| $Oligomer_3$ | 3' AACCCCGACGTCACG 5' | (SEQ ID No. 33) |
| $Oligomer_4$ | 3' TTCCGGACCCACGGA 5' | (SEQ ID No. 34) |
| $Oligomer_5$ | 3' CGAGGTACAGGCCCC 5' | (SEQ ID No. 35) |
| $Oligomer_6$ | 3' TACTCGAGTGTCTCG 5' | (SEQ ID No. 36) |
| $Oligomer_7$ | 3' ACGACCGTCCCTAGT 5' | (SEQ ID No. 37) |
| $Oligomer_8$ | 3' GACCGTGACTTCACC 5' | (SEQ ID No. 38) |
| $Oligomer_9$ | 3' TGACGGACGCCCGGA 5' | (SEQ ID No. 39) |
| $Oligomer_{10}$ | 3' CAGTCCTCGTCTAGC 5' | (SEQ ID No. 40) |
| $Oligomer_{11}$ | 3' TTCGACGTGAGTCCC 5' | (SEQ ID No. 41) |
| $Oligomer_{12}$ | 3' TCTCGGAGTCCCTTC 5' | (SEQ ID No. 42) |
| $Oligomer_{13}$ | 3' GGAGAGTCTGGTCGA 5' | (SEQ ID No. 43) |
| $Oligomer_{14}$ | 3' GGTCGGGTCGCGGGT 5' | (SEQ ID No. 44) |

Oligomers are complementary (antiparallel) to NbHOT Homo sapiens mRNA (clone 741045 accession number AA402345) which is specific to ovarian tumour cells. The distance of the oligomers each from other is nuN nucleotides of the NbHOT Homo sapiens mRNA.

```
Oligomer1-PA1 is    MEEPQSDPSVEPPLSQETFSDLWKLLPENNVL          (SEQ ID No. 3)
                                                  L^2
                    3' ATGGGCGGTAGGTAC 5'                     (SEQ ID No. 31)

Oligomer2-PA2 is    (K^1)SPLPSQAMDDLMLSPDDIEQWF               (SEQ ID No. 4)
                         L^1                   L^2
                    3' TAGCGGTGCCCTCGA 5'                     (SEQ ID No. 32)

Oligomer3-PA3 is    (K^1)TEDPGPDEAPRMPEAAPRVAPAPAAP           (SEQ ID No. 5)
                          L^1                      L^2
                    3' AACCCCGACGTCACG 5'                     (SEQ ID No. 33)

Oligomer4-PA4 is    (K^1)TPAAPAPAPSWPLSSSVPSQKTYQG            (SEQ ID No. 6)
                          L^1                    L^2
                    3' TTCCGGACCCACGGA 5'                     (SEQ ID No. 34)

Oligomer5-PA5 is    (K^1)SYGFRLGFLHSGTAKSVTCTY                (SEQ ID No. 7)
                          L^1                L^2
                    3' CGAGGTACAGGCCCC 5'                     (SEQ ID No. 35)
```

-continued

| | | |
|---|---|---|
| Oligomer$_6$-PA$_6$ is | (K^1)SPALNKMFCQLAKTCPVQLWVDSTPPPG<br>　　　　L^1　　　　　　　　　　　　L^2 | (SEQ ID No. 8) |
| | 3 TACTCGAGTGTCTCG 5' | (SEQ ID No. 36) |
| Oligomer$_7$-PA$_7$ is | (K^1)TRVRAMAIYKOSQHMTEVVRRCPHHE<br>　　　　L^1　　　　　　　　　　　L^2 | (SEQ ID No. 9) |
| | 3' ACGACCGTCCCTAGT 5' | (SEQ ID No. 37) |
| Oligomer$_8$-PA$_8$ is | (K^1)TCSDSDGLAPPQHLIRVEGNLRVEYLDDRRN<br>　　　　L^1　　　　　　　　　　　　　　L^2 | (SEQ ID No. 10) |
| | 3' GACCGTGACTTCACC 5' | (SEQ ID No. 38) |
| Oligomer$_9$-PA$_9$ is | (K^1)TFRHSVVVPYEPPEVGSDCTTIHYNYMCNS<br>　　　　L^1　　　　　　　　　　　　　L^2 | (SEQ ID No. 11) |
| | 3' TGACGGACGCCCGGA 5' | (SEQ ID No. 39) |
| Oligomer$_{10}$-PA$_{10}$ is | (K^1)SCMGGMNRRPILTIITLEDSSGNLLGRNS<br>　　　　L^1　　　　　　　　　　　　L^2 | (SEQ ID No. 12) |
| | 3' CAGTCCTCGTCTAGC 5' | (SEQ ID No. 40) |
| Oligomer$_{11}$-PA$_{11}$ is | (K^1)FEVRVCACPGRDRRTEEENLRKKGEPHHELPPGS<br>　　　　L^1　　　　　　　　　　　　　　　　L^2 | (SEQ ID No. 13) |
| | 3' TTCGACGTGAGTCCC 5' | (SEQ ID No. 41) |
| Oligomer$_{12}$-PA$_{12}$ is | (K^1)TKRALPNNTSSSPQPKKKPLDGEYF<br>　　　　L^1　　　　　　　　　　L^2 | (SEQ ID No. 14) |
| | 3' TCTCGGAGTCCCTTC5' | (SEQ ID No. 42) |
| Oligomer$_{13}$-PA$_{13}$ is | (K^1)TLQIRGRERFEMFRELNEALELKDAQAGKEPGG<br>　　　　L^1　　　　　　　　　　　　　　　L^2 | (SEQ ID No. 15) |
| | 3' GGAGAGTCTGGTCGA 5' | (SEQ ID No. 43) |
| Oligomer$_{14}$-PA$_{14}$ is | (K^1)SRAHSSHLKSKKGQSTSRHKKLMFKTEGPDSD<br>　　　　L^1 | (SEQ ID No. 16) |
| | 3' GGTCGGGTCGCGGGT 5' | (SEQ ID No. 44) |

This method of protein synthesis also allows modification of the synthesized protein. Certain aminoacids of the peptides used in the synthesis can be glycosylated or phosphorylated.

Glycosylation of a protein is a complex process, and difficulties may occur in the penetrance of some tissues with the glycosylated form of the peptide due to the size of the molecule.

However the use of phosphorylated peptides opens up the possibility to synthesize already active proteins in the cells of living organisms.

The Synthesis of RNA.

Using the method described above, it is possible to synthesise into targeted cells not only proteins but also RNAs. An example of such synthesis is represented in FIG. 10

To synthesize whole RNA in cells from n oligomers bound to oligoribonucleotides (oligomer-PAs) the concentration of such oligomer-PAs must be high. After the simultaneous hybridization of oligomer-PAs to the same molecule of the cellular RNA, the chemically active 3' hydroxyl group of the oligoribonucleotid PA$_1$ interacts with the linking moiety -L^2-S— which bound oligoribonucleotide PA$_2$ with oligomer 2. In this case the linking group is represented with a n —S-L^2-moiety which is coupled to phosphate group of the oligoribonucleotide PA$_2$. The 3' hydroxyl group of the oligoribonucleotide PA$_1$ interacts with the linking group of PA$_2$ forming a chemical bond with the phosphate group, releasing the oligoribonucleotide PA$_2$ at it's 5' end from oligomer 2, and activating the linking moiety with the formation of the —SH group. This chemically active group —SH interacts with linking moiety -L^1-S which couples the oligomers. This process is repeated n-1 times to bind all PAs in one molecule. PA$_1$ is bound through chemical moiety —O— to PA$_2$, then in turn PA$_1$-m-PA$_2$ is bound through chemical moiety —O— to PA$_3$, then PA$_1$-m-PA$_2$-m-PA$_3$ is bound through chemical moiety —O— to PA$_4$ and so on until the last oligoribonucleotide is bound, forming whole biologically active RNA.

In this figure "PA$_n$" are oligoribonucleotides comprising from 3 to 300 nucleotides.

n in "PA$_n$" means the ordinal number in a series of oligoribonucleotides used in the synthesis of a whole RNA, where n is selected from 2 to 1000.

What is claimed is:

1. A process for synthesis of biologically active compounds from biologically inactive precursors with the aim to deliver said biologically active compounds to the target cells having specific RNA or DNA molecules, the process comprising:

using a composition comprising at least two different oligomers chemically bound at their 5' and/or 3' end via a linking moiety to said biologically inactive precursors of biologically active compound, and said biologically inactive precursors comprising chemically active groups wherein said oligomers allow the hybridisation to a cellular RNA, DNA or dsDNA such that after hybridisation the distance between the 3' or 5' ends of said two oligomers coupled to the biologically inactive precursors is in the range of 0 to 8 ribo(deoxy) nucleotides and said hybridisation leads to a chemical coupling of said two precursors via said chemically active groups and/or said linking moieties and the intracellular synthesis of said biologically active compound in the target cells.

2. The process of claim 1, wherein said chemically active group of said biologically inactive precursor is selected from the group consisting of —NH(2)-, —NH—, —OH, —SH, —F, —CL, —Br, —I, and —R^1-C(X)—X^1-R^2, wherein R^1 and R^2 are independently chemical bond, alkyl, alkenyl, alkynyl, aryl, heteroalkyl, heteroalkenyl, heteroalkynyl, heteroaryl, cycloheteroaryl, carbocyclic, heterocyclic ring, X^1-P(X)(X)—X^1, —S(O)—, —S(O)(O)—, —X^1, —C(O)—, —N(H)—, —N=N—, —X^1-P(X)(X)—X^1-, —X^1-P(X)(X)—X^1-P(X)(X)—X^1, —X^1-P(X)(X)—X^1-P(X)(X)—X^1-P(X)(X)—X^1, —C(s)—, any suitable linking group: wherein X is independently S, O, NH, Se, alkyl, alkenyl, alkynyl: X^1 is independently S, O, NH, Se, alkyl, alkenyl, alkynyl.

3. The process of claim 1, wherein said at least two biologically inactive precursors are coupled via a chemical bond selected from the group consisting of: —S—S—, —O—, —NH—C(O)—, —C(O)—NH—, —C(O)O—, —C(O)—S—, —S—, —C(S)S—, —C(S)O—.

4. The process of claim 1, wherein said oligomers are selected from the group consisting of oligomers 2 to 14.

5. The process of claim 1, wherein said linking moiety connecting said oligomer to said biologically inactive precursor is selected from the group consisting of: L^2 is independently: chemical bond, —R^1-, —R^1-O—S—R^2-, —R^1-S—O—R^2-, R^1-S—S—R^2-, R^1-S—N(H)—R^2-, —R^1-N(H)—S—R^2-, —R^1-O—N(H)—R^2-, R^1-N(H)—O—R^2-, —R^1-C(X)—X^1-R^2-, —R^1-X—C(X)—X—C(X)—X—R^2-; wherein R^1 is independently: chemical bond, alkyl, alkenyl, alkynyl, aryl, heteroalkyl, heteroalkenyl, heteroalkynyl, heteroaryl, cycloheteroaryl, carbocyclic, heterocyclic ring, X^1-P(X)(X)—X^1, —S(O)—, —S(O)(O)—, -111 X^1-S(X)(X)—X^1-, —C(O)—, —N(H)—, —N=N—, —X^1-P(X)(X)—X^1-, —X^1-P(X)(X)—X^1-P(X)(X)—X^1-, —X^1-P(X)(X)—X^1, -P(X)(X)—X^1-P(X)(X)—X^1, —C(S)—, any suitable linking group: wherein R^2 is independently chemical bond, alkyl, alkenyl, alkynyl, aryl, heteroalkyl, heteroalkenyl, heteroalkynyl, heteroaryl, cycloheteroaryl, carbocyclic, heterocyclic ring, X^1-P(X)(X)—X^1, —S(O)—, S(O)(O)—, —X^1-S(X)(X)—X^1, —C(O)—, —N(H)—, —N=N—, —X^1-P(X)(X)—X^1-, —X^1-P(X)(X)—X^1-P(X)(X)—X^1, —X^1-P(X)(X)—X^1-P(X)(X)—X^1 -P(X)(X)—X^1 , —C(S)—, any suitable linking group: wherein X is independently S, O, NH, Se, alkyl, alkenyl, alkynyl: X^1 is independently S. 0, NH, Se. alkyl, alkenyl. alkynyl.

6. The process of claim 1, wherein the said biologically inactive precursors are peptides comprising from 2 to 100 aminoacids.

7. The process of claim 1, wherein said biologically active compound is selected from the group consisting of: proteins, enzymes, peptides, cyclic peptides, toxic peptides, modified toxic peptides and toxic proteins.

8. The process of claim 1, wherein said biologically active compound is daphnoretin, amanitin, D-actinomicin, ochratoxin A, or ergotamin.

* * * * *

SEQUENCE LISTING

<160> NUMBER OF SEQ ID NOS: 44

<210> SEQ ID NO 1
<211> LENGTH: 16
<212> TYPE: DNA
<213> ORGANISM: Human immunodeficiency virus type 1
<300> PUBLICATION INFORMATION:

-continued

```
<308> DATABASE ACCESSION NUMBER: X01762
<309> DATABASE ENTRY DATE: 1985-01-01
<310> PATENT DOCUMENT NUMBER: US 5,571,937
<311> PATENT FILING DATE: 1994-05-13
<312> PUBLICATION DATE: 1996-01-11
<313> RELEVANT RESIDUES: (1)..(16)

<400> SEQUENCE: 1
gaaggaatag aagaag                                                    16

<210> SEQ ID NO 2
<211> LENGTH: 16
<212> TYPE: DNA
<213> ORGANISM: Human immunodeficiency virus type 1
<300> PUBLICATION INFORMATION:
<302> TITLE: Complementary DNA and Toxins (seq ID 43)
<308> DATABASE ACCESSION NUMBER: X01762
<309> DATABASE ENTRY DATE: 1985-01-01
<310> PATENT DOCUMENT NUMBER: US 5,571,937
<311> PATENT FILING DATE: 1994-05-13
<312> PUBLICATION DATE: 1996-05-11
<313> RELEVANT RESIDUES: (17)..(32)

<400> SEQUENCE: 2
aaggtggaga gagaga                                                    16

<210> SEQ ID NO 3
<211> LENGTH: 32
<212> TYPE: PRT
<213> ORGANISM: Homo sapiens
<220> FEATURE:
<223> OTHER INFORMATION: part of the amino acid sequence of the Human
      tumour supressor p53
<300> PUBLICATION INFORMATION:
<301> AUTHORS: Harlow,E., Williamson,N.M., Ralston,R., Helfman,D.M. and
      Adams,T.E.
<302> TITLE: Molecular cloning and in vitro expression of a cDNA clone
      for human cellular tumor antigen p53
<303> JOURNAL: Molecular and cellular biology
<304> VOLUME: 5
<305> ISSUE: 7
<306> PAGES: 1601-1610
<307> DATE: 1985-07-01
<308> DATABASE ACCESSION NUMBER: K03199
<309> DATABASE ENTRY DATE: 1995-01-07

<400> SEQUENCE: 3

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

<210> SEQ ID NO 4
<211> LENGTH: 22
<212> TYPE: PRT
<213> ORGANISM: Homo sapiens
<220> FEATURE:
<223> OTHER INFORMATION: part of the amino acid sequence of the Human
      tumour supressor p53
<300> PUBLICATION INFORMATION:
<301> AUTHORS: Harlow,E., Williamson,N.M., Ralston,R., Helfman,D.M. and
      Adams,T.E.
<302> TITLE: Molecular cloning and in vitro expression of a cDNA clone
      for human cellular tumor antigen p53
<303> JOURNAL: Molecular and cellular biology
<304> VOLUME: 5
<305> ISSUE: 7
<306> PAGES: 1601-10
<307> DATE: 1985-06-01
<308> DATABASE ACCESSION NUMBER: K03199
<309> DATABASE ENTRY DATE: 1995-01-07
```

-continued

```
<400> SEQUENCE: 4

Ser Pro Leu Pro Ser Gln Ala Met Asp Asp Leu Met Leu Ser Pro Asp
1               5                   10                  15

Asp Ile Glu Gln Trp Phe
            20

<210> SEQ ID NO 5
<211> LENGTH: 26
<212> TYPE: PRT
<213> ORGANISM: Homo sapiens
<220> FEATURE:
<223> OTHER INFORMATION: part of the amino acid sequence of the Human
      tumour supressor p53
<300> PUBLICATION INFORMATION:
<301> AUTHORS: Harlow,E., Williamson,N.M., Ralston,R., Helfman,D.M. and
      Adams,T.E.
<302> TITLE: Molecular cloning and in vitro expression of a cDNA clone
      for human cellular tumor antigen p53
<303> JOURNAL: Molecular and cellular biology
<304> VOLUME: 5
<305> ISSUE: 7
<306> PAGES: 1601-10
<307> DATE: 1985-01-07
<308> DATABASE ACCESSION NUMBER: K03199
<309> DATABASE ENTRY DATE: 1995-07-01

<400> SEQUENCE: 5

Thr Glu Asp Pro Gly Pro Asp Glu Ala Pro Arg Met Pro Glu Ala Ala
1               5                   10                  15

Pro Arg Val Ala Pro Ala Pro Ala Ala Pro
            20                  25

<210> SEQ ID NO 6
<211> LENGTH: 25
<212> TYPE: PRT
<213> ORGANISM: Homo sapiens
<220> FEATURE:
<223> OTHER INFORMATION: part of the amino acid sequence of the Human
      tumour supressor p53
<300> PUBLICATION INFORMATION:
<301> AUTHORS: Harlow,E., Williamson,N.M., Ralston,R., Helfman,D.M. and
      Adams,T.E.
<302> TITLE: Molecular cloning and in vitro expression of a cDNA clone
      for human cellular tumor antigen p53
<303> JOURNAL: Molecular and cellular biology
<304> VOLUME: 5
<305> ISSUE: 7
<306> PAGES: 1601-10
<307> DATE: 1985-01-07
<308> DATABASE ACCESSION NUMBER: K03199
<309> DATABASE ENTRY DATE: 1995-07-01

<400> SEQUENCE: 6

Thr Pro Ala Ala Pro Ala Pro Ala Pro Ser Trp Pro Leu Ser Ser Ser
1               5                   10                  15

Val Pro Ser Gln Lys Thr Tyr Gln Gly
            20                  25

<210> SEQ ID NO 7
<211> LENGTH: 21
<212> TYPE: PRT
<213> ORGANISM: Homo sapiens
<220> FEATURE:
<223> OTHER INFORMATION: part of the amino acid sequence of the Human
      tumour supressor p53
<300> PUBLICATION INFORMATION:
<301> AUTHORS: Harlow,E., Williamson,N.M., Ralston,R., Helfman,D.M. and
      Adams,T.E.
<302> TITLE: Molecular cloning and in vitro expression of a cDNA clone
      for human cellular tumor antigen p53
```

-continued

```
<303> JOURNAL: Molecular and cellular biology
<304> VOLUME: 5
<305> ISSUE: 7
<306> PAGES: 1601-10
<307> DATE: 1985-01-07
<308> DATABASE ACCESSION NUMBER: K03199
<309> DATABASE ENTRY DATE: 1995-07-01

<400> SEQUENCE: 7

Ser Tyr Gly Phe Arg Leu Gly Phe Leu His Ser Gly Thr Ala Lys Ser
1               5                   10                  15

Val Thr Cys Thr Tyr
            20

<210> SEQ ID NO 8
<211> LENGTH: 28
<212> TYPE: PRT
<213> ORGANISM: Homo sapiens
<220> FEATURE:
<223> OTHER INFORMATION: part of the amino acid sequence of the Human
      tumour supressor p53
<300> PUBLICATION INFORMATION:
<301> AUTHORS: Harlow,E., Williamson,N.M., Ralston,R., Helfman,D.M. and
      Adams,T.E.
<302> TITLE: Molecular cloning and in vitro expression of a cDNA clone
      for human cellular tumor antigen p53
<303> JOURNAL: Molecular and cellular biology
<304> VOLUME: 5
<305> ISSUE: 7
<306> PAGES: 1601-10
<307> DATE: 1985-01-07
<308> DATABASE ACCESSION NUMBER: K03199
<309> DATABASE ENTRY DATE: 1995-07-01

<400> SEQUENCE: 8

Ser Pro Ala Leu Asn Lys Met Phe Cys Gln Leu Ala Lys Thr Cys Pro
1               5                   10                  15

Val Gln Leu Trp Val Asp Ser Thr Pro Pro Gly
            20                  25

<210> SEQ ID NO 9
<211> LENGTH: 26
<212> TYPE: PRT
<213> ORGANISM: Homo sapiens
<220> FEATURE:
<223> OTHER INFORMATION: part of the amino acid sequence of the Human
      tumour supressor p53
<300> PUBLICATION INFORMATION:
<301> AUTHORS: Harlow,E., Williamson,N.M., Ralston,R., Helfman,D.M. and
      Adams,T.E.
<302> TITLE: Molecular cloning and in vitro expression of a cDNA clone
      for human cellular tumor antigen p53
<303> JOURNAL: Molecular and cellular biology
<304> VOLUME: 5
<305> ISSUE: 7
<306> PAGES: 1601-10
<307> DATE: 1985-01-07
<308> DATABASE ACCESSION NUMBER: K03199
<309> DATABASE ENTRY DATE: 1995-07-01

<400> SEQUENCE: 9

Thr Arg Val Arg Ala Met Ala Ile Tyr Lys Gln Ser Gln His Met Thr
1               5                   10                  15

Glu Val Val Arg Arg Cys Pro His His Glu
            20                  25

<210> SEQ ID NO 10
<211> LENGTH: 30
<212> TYPE: PRT
<213> ORGANISM: Homo sapiens
```

```
<220> FEATURE:
<223> OTHER INFORMATION: part of the amino acid sequence of the Human
      tumour supressor p53
<300> PUBLICATION INFORMATION:
<301> AUTHORS: Harlow,E., Williamson,N.M., Ralston,R., Helfman,D.M. and
      Adams,T.E.
<302> TITLE: Molecular cloning and in vitro expression of a cDNA clone
      for human cellular tumor antigen p53
<303> JOURNAL: Molecular and cellular biology
<304> VOLUME: 5
<305> ISSUE: 7
<306> PAGES: 1601-10
<307> DATE: 1985-01-07
<308> DATABASE ACCESSION NUMBER: K03199
<309> DATABASE ENTRY DATE: 1995-07-01

<400> SEQUENCE: 10

Thr Cys Ser Asp Ser Asp Gly Leu Ala Pro Pro Gln His Leu Ile Arg
1               5                   10                  15

Val Glu Gly Asn Leu Arg Val Glu Tyr Leu Asp Asp Arg Asn
            20                  25                  30

<210> SEQ ID NO 11
<211> LENGTH: 30
<212> TYPE: PRT
<213> ORGANISM: Homo sapiens
<220> FEATURE:
<223> OTHER INFORMATION: part of the amino acid sequence of the Human
      tumour supressor p53
<300> PUBLICATION INFORMATION:
<301> AUTHORS: Harlow,E., Williamson,N.M., Ralston,R., Helfman,D.M. and
      Adams,T.E.
<302> TITLE: Molecular cloning and in vitro expression of a cDNA clone
      for human cellular tumor antigen p53
<303> JOURNAL: Molecular and cellular biology
<304> VOLUME: 5
<305> ISSUE: 7
<306> PAGES: 1601-10
<307> DATE: 1985-01-07
<308> DATABASE ACCESSION NUMBER: K03199
<309> DATABASE ENTRY DATE: 1995-07-01

<400> SEQUENCE: 11

Thr Phe Arg His Ser Val Val Val Pro Tyr Glu Pro Pro Glu Val Gly
1               5                   10                  15

Ser Asp Cys Thr Thr Ile His Tyr Asn Tyr Met Cys Asn Ser
            20                  25                  30

<210> SEQ ID NO 12
<211> LENGTH: 28
<212> TYPE: PRT
<213> ORGANISM: Homo sapiens
<220> FEATURE:
<223> OTHER INFORMATION: part of the amino acid sequence of the Human
      tumour supressor p53
<300> PUBLICATION INFORMATION:
<301> AUTHORS: Harlow,E., Williamson,N.M., Ralston,R., Helfman,D.M. and
      Adams,T.E.
<302> TITLE: Molecular cloning and in vitro expression of a cDNA clone
      for human cellular tumor antigen p53
<303> JOURNAL: Molecular and cellular biology
<304> VOLUME: 5
<305> ISSUE: 7
<306> PAGES: 1601-10
<307> DATE: 1985-01-07
<308> DATABASE ACCESSION NUMBER: K03199
<309> DATABASE ENTRY DATE: 1995-07-01

<400> SEQUENCE: 12

Ser Cys Met Gly Gly Met Asn Arg Arg Pro Ile Leu Thr Ile Ile Thr
1               5                   10                  15
```

-continued

```
Leu Glu Asp Ser Ser Gly Asn Leu Leu Gly Arg Asn
            20                  25

<210> SEQ ID NO 13
<211> LENGTH: 34
<212> TYPE: PRT
<213> ORGANISM: Homo sapiens
<220> FEATURE:
<223> OTHER INFORMATION: part of the amino acid sequence of the Human
      tumour supressor p53
<300> PUBLICATION INFORMATION:
<301> AUTHORS: Harlow,E., Williamson,N.M., Ralston,R., Helfman,D.M. and
      Adams,T.E.
<302> TITLE: Molecular cloning and in vitro expression of a cDNA clone
      for human cellular tumor antigen p53
<303> JOURNAL: Molecular and cellular biology
<304> VOLUME: 5
<305> ISSUE: 7
<306> PAGES: 1601-10
<307> DATE: 1985-01-07
<308> DATABASE ACCESSION NUMBER: K03199
<309> DATABASE ENTRY DATE: 1995-07-01

<400> SEQUENCE: 13

Ser Phe Glu Val Arg Val Cys Ala Cys Pro Gly Arg Asp Arg Arg Thr
1               5                   10                  15

Glu Glu Glu Asn Leu Arg Lys Lys Gly Glu Pro His His Glu Leu Pro
            20                  25                  30

Pro Gly

<210> SEQ ID NO 14
<211> LENGTH: 26
<212> TYPE: PRT
<213> ORGANISM: Homo sapiens
<220> FEATURE:
<223> OTHER INFORMATION: part of the amino acid sequence of the Human
      tumour supressor p53
<300> PUBLICATION INFORMATION:
<301> AUTHORS: Harlow,E., Williamson,N.M., Ralston,R., Helfman,D.M. and
      Adams,T.E.
<302> TITLE: Molecular cloning and in vitro expression of a cDNA clone
      for human cellular tumor antigen p53
<303> JOURNAL: Molecular and cellular biology
<304> VOLUME: 5
<305> ISSUE: 7
<306> PAGES: 1601-10
<307> DATE: 1985-01-07
<308> DATABASE ACCESSION NUMBER: K03199
<309> DATABASE ENTRY DATE: 1995-07-01

<400> SEQUENCE: 14

Ser Thr Lys Arg Ala Leu Pro Asn Asn Thr Ser Ser Pro Gln Pro
1               5                   10                  15

Lys Lys Lys Pro Leu Asp Gly Glu Tyr Phe
            20                  25

<210> SEQ ID NO 15
<211> LENGTH: 33
<212> TYPE: PRT
<213> ORGANISM: Homo sapiens
<220> FEATURE:
<223> OTHER INFORMATION: part of the amino acid sequence of the Human
      tumour supressor p53
<300> PUBLICATION INFORMATION:
<301> AUTHORS: Harlow,E., Williamson,N.M., Ralston,R., Helfman,D.M. and
      Adams,T.E.
<302> TITLE: Molecular cloning and in vitro expression of a cDNA clone
      for human cellular tumor antigen p53
<303> JOURNAL: Molecular and cellular biology
<304> VOLUME: 5
<305> ISSUE: 7
```

```
<306> PAGES: 1601-10
<307> DATE: 1985-01-07
<308> DATABASE ACCESSION NUMBER: K03199
<309> DATABASE ENTRY DATE: 1995-07-01

<400> SEQUENCE: 15

Thr Leu Gln Ile Arg Gly Arg Glu Arg Phe Glu Met Phe Arg Glu Leu
1               5                  10                 15

Asn Glu Ala Leu Glu Leu Lys Asp Ala Gln Ala Gly Lys Glu Pro Gly
             20                  25                 30

Gly

<210> SEQ ID NO 16
<211> LENGTH: 32
<212> TYPE: PRT
<213> ORGANISM: Homo sapiens
<220> FEATURE:
<223> OTHER INFORMATION: part of the amino acid sequence of the Human
      tumour supressor p53
<300> PUBLICATION INFORMATION:
<301> AUTHORS: Harlow,E., Williamson,N.M., Ralston,R., Helfman,D.M. and
      Adams,T.E.
<302> TITLE: Molecular cloning and in vitro expression of a cDNA clone
      for human cellular tumor antigen p53
<303> JOURNAL: Molecular and cellular biology
<304> VOLUME: 5
<305> ISSUE: 7
<306> PAGES: 1601-10
<307> DATE: 1985-01-07
<308> DATABASE ACCESSION NUMBER: K03199
<309> DATABASE ENTRY DATE: 1995-07-01

<400> SEQUENCE: 16

Ser Arg Ala His Ser Ser His Leu Lys Ser Lys Lys Gly Gln Ser Thr
1               5                  10                 15

Ser Arg His Lys Lys Leu Met Phe Lys Thr Glu Gly Pro Asp Ser Asp
             20                  25                 30

<210> SEQ ID NO 17
<211> LENGTH: 21
<212> TYPE: DNA
<213> ORGANISM: Homo sapiens
<220> FEATURE:
<223> OTHER INFORMATION: antisense to the human tissue plasminogen
      activator mRNA
<300> PUBLICATION INFORMATION:
<301> AUTHORS: Degen,S.J., Rajput,B. and Reich,E.
<302> TITLE: The human tissue plasminogen activator gene
<303> JOURNAL: Journal of Biological Chemistry
<304> VOLUME: 261
<305> ISSUE: 15
<306> PAGES: 6972-85
<307> DATE: 1986-05-25
<308> DATABASE ACCESSION NUMBER: K03021
<309> DATABASE ENTRY DATE: 1986-04-08

<400> SEQUENCE: 17
cccaatccct cttgcaactg a                                         21

<210> SEQ ID NO 18
<211> LENGTH: 22
<212> TYPE: DNA
<213> ORGANISM: Homo sapiens
<220> FEATURE:
<223> OTHER INFORMATION: antisense to the human tissue plasminogen
      activator mRNA
<300> PUBLICATION INFORMATION:
<301> AUTHORS: Degen,S.J., Rajput,B. and Reich,E.
<302> TITLE: The human tissue plasminogen activator gene
<303> JOURNAL: Journal of Biological Chemistry
```

-continued

```
<304> VOLUME: 261
<305> ISSUE: 15
<306> PAGES: 6972-85
<307> DATE: 1986-05-25
<308> DATABASE ACCESSION NUMBER: K03021
<309> DATABASE ENTRY DATE: 1986-04-08

<400> SEQUENCE: 18
attctactac aagtctgccc tt                                              22

<210> SEQ ID NO 19
<211> LENGTH: 18
<212> TYPE: DNA
<213> ORGANISM: Homo sapiens
<220> FEATURE:
<223> OTHER INFORMATION: antisense to the human tissue plasminogen
      activator mRNA
<300> PUBLICATION INFORMATION:
<301> AUTHORS: Degen,S.J., Rajput,B. and Reich,E.
<302> TITLE: The human tissue plasminogen activator gene
<303> JOURNAL: Journal of Biological Chemistry
<304> VOLUME: 261
<305> ISSUE: 15
<306> PAGES: 6972-85
<307> DATE: 1986-05-25
<308> DATABASE ACCESSION NUMBER: K03021
<309> DATABASE ENTRY DATE: 1986-04-08

<400> SEQUENCE: 19
ttgtgaccgg ctccactg                                                   18

<210> SEQ ID NO 20
<211> LENGTH: 19
<212> TYPE: DNA
<213> ORGANISM: Homo sapiens
<220> FEATURE:
<223> OTHER INFORMATION: antisense to the human tissue plasminogen
      activator mRNA
<300> PUBLICATION INFORMATION:
<301> AUTHORS: Degen,S.J., Rajput,B. and Reich,E.
<302> TITLE: The human tissue plasminogen activator gene
<303> JOURNAL: Journal of Biological Chemistry
<304> VOLUME: 261
<305> ISSUE: 15
<306> PAGES: 6972-85
<307> DATE: 1986-05-25
<308> DATABASE ACCESSION NUMBER: K03021
<309> DATABASE ENTRY DATE: 1986-04-08

<400> SEQUENCE: 20
taccttggta cttctctaa                                                  19

<210> SEQ ID NO 21
<211> LENGTH: 21
<212> TYPE: DNA
<213> ORGANISM: Homo sapiens
<220> FEATURE:
<223> OTHER INFORMATION: antisense to the human tissue plasminogen
      activator mRNA
<300> PUBLICATION INFORMATION:
<301> AUTHORS: Degen,S.J., Rajput,B. and Reich,E.
<302> TITLE: The human tissue plasminogen activator gene
<303> JOURNAL: Journal of Biological Chemistry
<304> VOLUME: 261
<305> ISSUE: 15
<306> PAGES: 6972-85
<307> DATE: 1986-05-25
<308> DATABASE ACCESSION NUMBER: K03021
<309> DATABASE ENTRY DATE: 1986-04-08

<400> SEQUENCE: 21
atgccatatt agcccatcag a                                               21
```

```
<210> SEQ ID NO 22
<211> LENGTH: 22
<212> TYPE: DNA
<213> ORGANISM: Homo sapiens
<220> FEATURE:
<223> OTHER INFORMATION: antisense to the human tissue plasminogen
      activator mRNA
<300> PUBLICATION INFORMATION:
<301> AUTHORS: Degen,S.J., Rajput,B. and Reich,E.
<302> TITLE: The human tissue plasminogen activator gene
<303> JOURNAL: Journal of Biological Chemistry
<304> VOLUME: 261
<305> ISSUE: 15
<306> PAGES: 6972-85
<307> DATE: 1986-05-25
<308> DATABASE ACCESSION NUMBER: K03021
<309> DATABASE ENTRY DATE: 1986-04-08

<400> SEQUENCE: 22
ccaagcattc tgtccctcct tt                                              22

<210> SEQ ID NO 23
<211> LENGTH: 17
<212> TYPE: DNA
<213> ORGANISM: Homo sapiens
<220> FEATURE:
<223> OTHER INFORMATION: antisense to the human tissue plasminogen
      activator mRNA
<300> PUBLICATION INFORMATION:
<301> AUTHORS: Degen,S.J., Rajput,B. and Reich,E.
<302> TITLE: The human tissue plasminogen activator gene
<303> JOURNAL: Journal of Biological Chemistry
<304> VOLUME: 261
<305> ISSUE: 15
<306> PAGES: 6972-85
<307> DATE: 1986-05-25
<308> DATABASE ACCESSION NUMBER: K03021
<309> DATABASE ENTRY DATE: 1986-04-08

<400> SEQUENCE: 23
tccggtccgg agcacca                                                    17

<210> SEQ ID NO 24
<211> LENGTH: 20
<212> TYPE: DNA
<213> ORGANISM: Homo sapiens
<220> FEATURE:
<223> OTHER INFORMATION: antisense to the human tissue plasminogen
      activator mRNA
<300> PUBLICATION INFORMATION:
<301> AUTHORS: Degen,S.J., Rajput,B. and Reich,E.
<302> TITLE: The human tissue plasminogen activator gene
<303> JOURNAL: Journal of Biological Chemistry
<304> VOLUME: 261
<305> ISSUE: 15
<306> PAGES: 6972-85
<307> DATE: 1986-05-25
<308> DATABASE ACCESSION NUMBER: K03021
<309> DATABASE ENTRY DATE: 1986-04-08

<400> SEQUENCE: 24
gccatgacct gtatgttaca                                                 20

<210> SEQ ID NO 25
<211> LENGTH: 20
<212> TYPE: DNA
<213> ORGANISM: Homo sapiens
<220> FEATURE:
<223> OTHER INFORMATION: antisense to the human tissue plasminogen
      activator mRNA
<300> PUBLICATION INFORMATION:
```

-continued

```
<301> AUTHORS: Degen,S.J., Rajput,B. and Reich,E.
<302> TITLE: The human tissue plasminogen activator gene
<303> JOURNAL: Journal of Biological Chemistry
<304> VOLUME: 261
<305> ISSUE: 15
<306> PAGES: 6972-85
<307> DATE: 1986-05-25
<308> DATABASE ACCESSION NUMBER: K03021
<309> DATABASE ENTRY DATE: 1986-04-08

<400> SEQUENCE: 25
ggtgtgggaa agttagcggg                                              20

<210> SEQ ID NO 26
<211> LENGTH: 21
<212> TYPE: DNA
<213> ORGANISM: Homo sapiens
<220> FEATURE:
<223> OTHER INFORMATION: antisense to the human tissue plasminogen
      activator mRNA
<300> PUBLICATION INFORMATION:
<301> AUTHORS: Degen,S.J., Rajput,B. and Reich,E.
<302> TITLE: The human tissue plasminogen activator gene
<303> JOURNAL: Journal of Biological Chemistry
<304> VOLUME: 261
<305> ISSUE: 15
<306> PAGES: 6972-85
<307> DATE: 1986-05-25
<308> DATABASE ACCESSION NUMBER: K03021
<309> DATABASE ENTRY DATE: 1986-04-08

<400> SEQUENCE: 26
gcgaattcca aatgatttta a                                            21

<210> SEQ ID NO 27
<211> LENGTH: 17
<212> TYPE: DNA
<213> ORGANISM: Homo sapiens
<220> FEATURE:
<223> OTHER INFORMATION: antisense to the human tissue plasminogen
      activator mRNA
<300> PUBLICATION INFORMATION:
<301> AUTHORS: Degen,S.J., Rajput,B. and Reich,E.
<302> TITLE: The human tissue plasminogen activator gene
<303> JOURNAL: Journal of Biological Chemistry
<304> VOLUME: 261
<305> ISSUE: 15
<306> PAGES: 6972-85
<307> DATE: 1986-05-25
<308> DATABASE ACCESSION NUMBER: K03021
<309> DATABASE ENTRY DATE: 1986-04-08

<400> SEQUENCE: 27
aatgtgaaca tgaataa                                                 17

<210> SEQ ID NO 28
<211> LENGTH: 22
<212> TYPE: DNA
<213> ORGANISM: Homo sapiens
<220> FEATURE:
<223> OTHER INFORMATION: antisense to the human tissue plasminogen
      activator mRNA
<300> PUBLICATION INFORMATION:
<301> AUTHORS: Degen,S.J., Rajput,B. and Reich,E.
<302> TITLE: The human tissue plasminogen activator gene
<303> JOURNAL: Journal of Biological Chemistry
<304> VOLUME: 261
<305> ISSUE: 15
<306> PAGES: 6972-85
<307> DATE: 1986-05-25
<308> DATABASE ACCESSION NUMBER: K03021
<309> DATABASE ENTRY DATE: 1986-04-08
```

```
<400> SEQUENCE: 28
agagtgggat acagcatcta ta                                          22

<210> SEQ ID NO 29
<211> LENGTH: 22
<212> TYPE: DNA
<213> ORGANISM: Homo sapiens
<220> FEATURE:
<223> OTHER INFORMATION: antisense to the human tissue plasminogen
      activator mRNA
<300> PUBLICATION INFORMATION:
<301> AUTHORS: Degen,S.J., Rajput,B. and Reich,E.
<302> TITLE: The human tissue plasminogen activator gene
<303> JOURNAL: Journal of Biological Chemistry
<304> VOLUME: 261
<305> ISSUE: 15
<306> PAGES: 6972-85
<307> DATE: 1986-05-25
<308> DATABASE ACCESSION NUMBER: K03021
<309> DATABASE ENTRY DATE: 1986-04-08

<400> SEQUENCE: 29
acaaaaccat tccactctga tt                                          22

<210> SEQ ID NO 30
<211> LENGTH: 19
<212> TYPE: DNA
<213> ORGANISM: Homo sapiens
<220> FEATURE:
<223> OTHER INFORMATION: antisense to the human tissue plasminogen
      activator mRNA
<300> PUBLICATION INFORMATION:
<301> AUTHORS: Degen,S.J., Rajput,B. and Reich,E.
<302> TITLE: The human tissue plasminogen activator gene
<303> JOURNAL: Journal of Biological Chemistry
<304> VOLUME: 261
<305> ISSUE: 15
<306> PAGES: 6972-85
<307> DATE: 1986-05-25
<308> DATABASE ACCESSION NUMBER: K03021
<309> DATABASE ENTRY DATE: 1986-04-08

<400> SEQUENCE: 30
ttggaaaaac tgtgaaaaa                                              19

<210> SEQ ID NO 31
<211> LENGTH: 15
<212> TYPE: DNA
<213> ORGANISM: Homo sapiens
<220> FEATURE:
<223> OTHER INFORMATION: Antisense to the human NbHOT (cyclin D) mRNA
<300> PUBLICATION INFORMATION:
<301> AUTHORS: Inaba,T., Matsushime,H., Valentine,M., Roussel,M.F.,
      Sherr,C.J. and Look,A.T
<302> TITLE: Genomic organization, chromosomal localization, and
      independent expression of human cyclin D genes
<303> JOURNAL: Genomics
<304> VOLUME: 13
<305> ISSUE: 3
<306> PAGES: 565-574
<307> DATE: 1992-07-01
<308> DATABASE ACCESSION NUMBER: NM_001760
<309> DATABASE ENTRY DATE: 2001-11-16
<300> PUBLICATION INFORMATION:
<308> DATABASE ACCESSION NUMBER: AA402345
<309> DATABASE ENTRY DATE: 1996-12-20

<400> SEQUENCE: 31
catggatggc gggta                                                  15

<210> SEQ ID NO 32
```

```
<211> LENGTH: 15
<212> TYPE: DNA
<213> ORGANISM: Homo sapiens
<220> FEATURE:
<223> OTHER INFORMATION: Antisense to the human NbHOT (cyclin D) mRNA
<300> PUBLICATION INFORMATION:
<301> AUTHORS: Inaba,T., Matsushime,H., Valentine,M., Roussel,M.F.,
      Sherr,C.J. and Look,A.T
<302> TITLE: Genomic organization, chromosomal localization, and
      independent expression of human cyclin D genes
<303> JOURNAL: Genomics
<304> VOLUME: 13
<305> ISSUE: 3
<306> PAGES: 565-574
<307> DATE: 1992-07-01
<308> DATABASE ACCESSION NUMBER: NM_001760
<309> DATABASE ENTRY DATE: 2001-11-16
<300> PUBLICATION INFORMATION:
<308> DATABASE ACCESSION NUMBER: AA402345
<309> DATABASE ENTRY DATE: 1996-12-20

<400> SEQUENCE: 32
agctcccgtg gcgat                                                    15

<210> SEQ ID NO 33
<211> LENGTH: 15
<212> TYPE: DNA
<213> ORGANISM: Homo sapiens
<220> FEATURE:
<223> OTHER INFORMATION: Antisense to the human NbHOT (cyclin D) mRNA
<300> PUBLICATION INFORMATION:
<301> AUTHORS: Inaba,T., Matsushime,H., Valentine,M., Roussel,M.F.,
      Sherr,C.J. and Look,A.T
<302> TITLE: Genomic organization, chromosomal localization, and
      independent expression of human cyclin D genes
<303> JOURNAL: Genomics
<304> VOLUME: 13
<305> ISSUE: 3
<306> PAGES: 565-574
<307> DATE: 1992-07-01
<308> DATABASE ACCESSION NUMBER: NM_001760
<309> DATABASE ENTRY DATE: 2001-11-16
<300> PUBLICATION INFORMATION:
<308> DATABASE ACCESSION NUMBER: AA402345
<309> DATABASE ENTRY DATE: 1996-12-20

<400> SEQUENCE: 33
gcactgcagc cccaa                                                    15

<210> SEQ ID NO 34
<211> LENGTH: 15
<212> TYPE: DNA
<213> ORGANISM: Homo sapiens
<220> FEATURE:
<223> OTHER INFORMATION: Antisense to the human NbHOT (cyclin D) mRNA
<300> PUBLICATION INFORMATION:
<301> AUTHORS: Inaba,T., Matsushime,H., Valentine,M., Roussel,M.F.,
      Sherr,C.J. and Look,A.T
<302> TITLE: Genomic organization, chromosomal localization, and
      independent expression of human cyclin D genes
<303> JOURNAL: Genomics
<304> VOLUME: 13
<305> ISSUE: 3
<306> PAGES: 565-574
<307> DATE: 1992-07-01
<308> DATABASE ACCESSION NUMBER: NM_001760
<309> DATABASE ENTRY DATE: 2001-11-16
<300> PUBLICATION INFORMATION:
<308> DATABASE ACCESSION NUMBER: AA402345
<309> DATABASE ENTRY DATE: 1996-12-20

<400> SEQUENCE: 34
aggcacccag gcctt                                                    15
```

```
<210> SEQ ID NO 35
<211> LENGTH: 15
<212> TYPE: DNA
<213> ORGANISM: Homo sapiens
<220> FEATURE:
<223> OTHER INFORMATION: Antisense to the human NbHOT (cyclin D) mRNA
<300> PUBLICATION INFORMATION:
<301> AUTHORS: Inaba,T., Matsushime,H., Valentine,M., Roussel,M.F.,
      Sherr,C.J.
      and Look,A.T
<302> TITLE: Genomic organization, chromosomal localization, and
      independent expression of human cyclin D genes
<303> JOURNAL: Genomics
<304> VOLUME: 13
<305> ISSUE: 3
<306> PAGES: 565-574
<307> DATE: 1992-07-01
<308> DATABASE ACCESSION NUMBER: NM_001760
<309> DATABASE ENTRY DATE: 2001-11-16
<300> PUBLICATION INFORMATION:
<308> DATABASE ACCESSION NUMBER: AA402345
<309> DATABASE ENTRY DATE: 1996-12-20

<400> SEQUENCE: 35
ccccggacat ggagc                                              15

<210> SEQ ID NO 36
<211> LENGTH: 15
<212> TYPE: DNA
<213> ORGANISM: Homo sapiens
<220> FEATURE:
<223> OTHER INFORMATION: Antisense to the human NbHOT (cyclin D) mRNA
<300> PUBLICATION INFORMATION:
<301> AUTHORS: Inaba,T., Matsushime,H., Valentine,M., Roussel,M.F.,
      Sherr,C.J. and Look,A.T
<302> TITLE: Genomic organization, chromosomal localization, and
      independent expression of human cyclin D genes
<303> JOURNAL: Genomics
<304> VOLUME: 13
<305> ISSUE: 3
<306> PAGES: 565-574
<307> DATE: 1992-07-01
<308> DATABASE ACCESSION NUMBER: NM_001760
<309> DATABASE ENTRY DATE: 2001-11-16
<300> PUBLICATION INFORMATION:
<308> DATABASE ACCESSION NUMBER: AA402345
<309> DATABASE ENTRY DATE: 1996-12-20

<400> SEQUENCE: 36
gctctgtgag ctcat                                              15

<210> SEQ ID NO 37
<211> LENGTH: 15
<212> TYPE: DNA
<213> ORGANISM: Homo sapiens
<220> FEATURE:
<223> OTHER INFORMATION: Antisense to the human NbHOT (cyclin D) mRNA
<300> PUBLICATION INFORMATION:
<301> AUTHORS: Inaba,T., Matsushime,H., Valentine,M., Roussel,M.F.,
      Sherr,C.J. and Look,A.T
<302> TITLE: Genomic organization, chromosomal localization, and
      independent expression of human cyclin D genes
<303> JOURNAL: Genomics
<304> VOLUME: 13
<305> ISSUE: 3
<306> PAGES: 565-574
<307> DATE: 1992-07-01
<308> DATABASE ACCESSION NUMBER: NM_001760
<309> DATABASE ENTRY DATE: 2001-11-16
<300> PUBLICATION INFORMATION:
<308> DATABASE ACCESSION NUMBER: AA402345
<309> DATABASE ENTRY DATE: 1996-12-20

<400> SEQUENCE: 37
```

```
tgatccctgc cagca                                                    15
```

<210> SEQ ID NO 38
<211> LENGTH: 15
<212> TYPE: DNA
<213> ORGANISM: Homo sapiens
<220> FEATURE:
<223> OTHER INFORMATION: Antisense to the human NbHOT (cyclin D) mRNA
<300> PUBLICATION INFORMATION:
<301> AUTHORS: Inaba,T., Matsushime,H., Valentine,M., Roussel,M.F.,
      Sherr,C.J. and Look,A.T
<302> TITLE: Genomic organization, chromosomal localization, and
      independent expression of human cyclin D genes
<303> JOURNAL: Genomics
<304> VOLUME: 13
<305> ISSUE: 3
<306> PAGES: 565-574
<307> DATE: 1992-07-01
<308> DATABASE ACCESSION NUMBER: NM_001760
<309> DATABASE ENTRY DATE: 2001-11-16
<300> PUBLICATION INFORMATION:
<308> DATABASE ACCESSION NUMBER: AA402345
<309> DATABASE ENTRY DATE: 1996-12-20

<400> SEQUENCE: 38

```
ccacttcagt gccag                                                    15
```

<210> SEQ ID NO 39
<211> LENGTH: 15
<212> TYPE: DNA
<213> ORGANISM: Homo sapiens
<220> FEATURE:
<223> OTHER INFORMATION: Antisense to the human NbHOT (cyclin D) mRNA
<300> PUBLICATION INFORMATION:
<301> AUTHORS: Inaba,T., Matsushime,H., Valentine,M., Roussel,M.F.,
      Sherr,C.J. and Look,A.T
<302> TITLE: Genomic organization, chromosomal localization, and
      independent expression of human cyclin D genes
<303> JOURNAL: Genomics
<304> VOLUME: 13
<305> ISSUE: 3
<306> PAGES: 565-574
<307> DATE: 1992-07-01
<308> DATABASE ACCESSION NUMBER: NM_001760
<309> DATABASE ENTRY DATE: 2001-11-16
<300> PUBLICATION INFORMATION:
<308> DATABASE ACCESSION NUMBER: AA402345
<309> DATABASE ENTRY DATE: 1996-12-20

<400> SEQUENCE: 39

```
aggcccgcag gcagt                                                    15
```

<210> SEQ ID NO 40
<211> LENGTH: 15
<212> TYPE: DNA
<213> ORGANISM: Homo sapiens
<220> FEATURE:
<223> OTHER INFORMATION: Antisense to the human NbHOT (cyclin D) mRNA
<300> PUBLICATION INFORMATION:
<301> AUTHORS: Inaba,T., Matsushime,H., Valentine,M., Roussel,M.F.,
      Sherr,C.J. and Look,A.T
<302> TITLE: Genomic organization, chromosomal localization, and
      independent expression of human cyclin D genes
<303> JOURNAL: Genomics
<304> VOLUME: 13
<305> ISSUE: 3
<306> PAGES: 565-574
<307> DATE: 1992-07-01
<308> DATABASE ACCESSION NUMBER: NM_001760
<309> DATABASE ENTRY DATE: 2001-11-16
<300> PUBLICATION INFORMATION:
<308> DATABASE ACCESSION NUMBER: AA402345
<309> DATABASE ENTRY DATE: 1996-12-20

-continued

```
<400> SEQUENCE: 40
cgatctgctc ctgac                                                    15

<210> SEQ ID NO 41
<211> LENGTH: 15
<212> TYPE: DNA
<213> ORGANISM: Homo sapiens
<220> FEATURE:
<223> OTHER INFORMATION: Antisense to the human NbHOT (cyclin D) mRNA
<300> PUBLICATION INFORMATION:
<301> AUTHORS: Inaba,T., Matsushime,H., Valentine,M., Roussel,M.F.,
      Sherr,C.J. and Look,A.T
<302> TITLE: Genomic organization, chromosomal localization, and
      independent expression of human cyclin D genes
<303> JOURNAL: Genomics
<304> VOLUME: 13
<305> ISSUE: 3
<306> PAGES: 565-574
<307> DATE: 1992-07-01
<308> DATABASE ACCESSION NUMBER: NM_001760
<309> DATABASE ENTRY DATE: 2001-11-16
<300> PUBLICATION INFORMATION:
<308> DATABASE ACCESSION NUMBER: AA402345
<309> DATABASE ENTRY DATE: 1996-12-20

<400> SEQUENCE: 41
ccctgagtgc agctt                                                    15

<210> SEQ ID NO 42
<211> LENGTH: 15
<212> TYPE: DNA
<213> ORGANISM: Homo sapiens
<220> FEATURE:
<223> OTHER INFORMATION: Antisense to the human NbHOT (cyclin D) mRNA
<300> PUBLICATION INFORMATION:
<301> AUTHORS: Inaba,T., Matsushime,H., Valentine,M., Roussel,M.F.,
      Sherr,C.J. and Look,A.T
<302> TITLE: Genomic organization, chromosomal localization, and
      independent expression of human cyclin D genes
<303> JOURNAL: Genomics
<304> VOLUME: 13
<305> ISSUE: 3
<306> PAGES: 565-574
<307> DATE: 1992-07-01
<308> DATABASE ACCESSION NUMBER: NM_001760
<309> DATABASE ENTRY DATE: 2001-11-16
<300> PUBLICATION INFORMATION:
<308> DATABASE ACCESSION NUMBER: AA402345
<309> DATABASE ENTRY DATE: 1996-12-20

<400> SEQUENCE: 42
cttccctgag gctct                                                    15

<210> SEQ ID NO 43
<211> LENGTH: 15
<212> TYPE: DNA
<213> ORGANISM: Homo sapiens
<220> FEATURE:
<223> OTHER INFORMATION: Antisense to the human NbHOT (cyclin D) mRNA
<300> PUBLICATION INFORMATION:
<301> AUTHORS: Inaba,T., Matsushime,H., Valentine,M., Roussel,M.F.,
      Sherr,C.J. and Look,A.T
<302> TITLE: Genomic organization, chromosomal localization, and
      independent expression of human cyclin D genes
<303> JOURNAL: Genomics
<304> VOLUME: 13
<305> ISSUE: 3
<306> PAGES: 565-574
<307> DATE: 1992-07-01
<308> DATABASE ACCESSION NUMBER: NM_001760
<309> DATABASE ENTRY DATE: 2001-11-16
<300> PUBLICATION INFORMATION:
```

```
<308> DATABASE ACCESSION NUMBER: AA402345
<309> DATABASE ENTRY DATE: 1996-12-20

<400> SEQUENCE: 43
agctggtctg agagg                                                    15

<210> SEQ ID NO 44
<211> LENGTH: 15
<212> TYPE: DNA
<213> ORGANISM: Homo sapiens
<220> FEATURE:
<223> OTHER INFORMATION: Antisense to the human NbHOT (cyclin D) mRNA
<300> PUBLICATION INFORMATION:
<301> AUTHORS: Inaba,T., Matsushime,H., Valentine,M., Roussel,M.F.,
      Sherr,C.J. and Look,A.T
<302> TITLE: Genomic organization, chromosomal localization, and
      independent expression of human cyclin D genes
<303> JOURNAL: Genomics
<304> VOLUME: 13
<305> ISSUE: 3
<306> PAGES: 565-574
<307> DATE: 1992-07-01
<308> DATABASE ACCESSION NUMBER: NM_001760
<309> DATABASE ENTRY DATE: 2001-11-16
<300> PUBLICATION INFORMATION:
<308> DATABASE ACCESSION NUMBER: AA402345
<309> DATABASE ENTRY DATE: 1996-12-20

<400> SEQUENCE: 44
tgggcgctgg gctgg                                                    15
```